US011083802B2

(12) United States Patent
Campbell et al.

(10) Patent No.: US 11,083,802 B2
(45) Date of Patent: Aug. 10, 2021

(54) ECHOLUCENT IMPLANT COMPOSITIONS AND METHODS

(71) Applicant: Incept, LLC, Lexington, MA (US)

(72) Inventors: Patrick Campbell, Belmont, MA (US); Amarpreet S. Sawhney, Lexington, MA (US)

(73) Assignee: Incept, LLC, Lexington, MA (US)

( * ) Notice: Subject to any disclaimer, the term of this patent is extended or adjusted under 35 U.S.C. 154(b) by 0 days.

(21) Appl. No.: 16/817,291

(22) Filed: Mar. 12, 2020

(65) Prior Publication Data

US 2020/0206365 A1  Jul. 2, 2020

Related U.S. Application Data

(60) Continuation of application No. 16/296,795, filed on Mar. 8, 2019, now Pat. No. 10,786,581, which is a
(Continued)

(51) Int. Cl.
*A61K 49/04* (2006.01)
*A61K 51/12* (2006.01)
(Continued)

(52) U.S. Cl.
CPC ...... *A61K 49/0442* (2013.01); *A61K 49/0419* (2013.01); *A61K 51/1244* (2013.01);
(Continued)

(58) Field of Classification Search
CPC ............ A61K 49/0442; A61K 49/0419; A61K 51/1244; A61K 2123/00; A61K 31/145;
(Continued)

(56) References Cited

U.S. PATENT DOCUMENTS 3,640,741 A  2/1972  Etes
3,865,108 A  2/1975  Hartop
(Continued)

FOREIGN PATENT DOCUMENTS

CA  2 188 464  11/1995
EP  1019446 B2  11/2011
(Continued)

OTHER PUBLICATIONS

Anscher et al., "Combined External Beam Irradiation and External Regional Hyperthermia for Locally Advanced Adenocarcinoma of The Prostate", International Journal of Radiation Oncology Biology Physics, vol. 37 (5):1059-1065 (1997).
(Continued)

*Primary Examiner* — Carlos A Azpuru
(74) *Attorney, Agent, or Firm* — Christensen, Fonder, Dardi & Herbert PLLC; Diane E. Bennett; Peter S. Dardi

(57) ABSTRACT

Implantable materials visible under ultrasound may delivered to a selected placement site and biodegrade after a certain period of time. Ultrasound visible implantable materials may be delivered through an applicator and may include ultrasound contrast agents and/or radiopaque agents. Applications include monitoring the delivery of an implant of the implantable materials to the placement site with ultrasound and delivery of therapeutic agents to a tissue at the placement site for treating a patient.

23 Claims, 9 Drawing Sheets

Related U.S. Application Data continuation of application No. 15/613,555, filed on Jun. 5, 2017, now Pat. No. 10,272,164, which is a continuation of application No. 15/066,707, filed on Mar. 10, 2016, now Pat. No. 9,669,117, which is a continuation of application No. 14/465,202, filed on Aug. 21, 2014, now Pat. No. 9,308,283, which is a division of application No. 13/750,570, filed on Jan. 25, 2013, now Pat. No. 8,852,646, which is a division of application No. 12/968,527, filed on Dec. 15, 2010, now Pat. No. 8,383,161.

(60) Provisional application No. 61/286,450, filed on Dec. 15, 2009.

(51) Int. Cl.
  *A61L 27/50* (2006.01)
  *A61L 27/52* (2006.01)
  *A61L 27/58* (2006.01)
  *A61L 31/14* (2006.01)
  *A61L 31/18* (2006.01)

(52) U.S. Cl.
  CPC .............. *A61L 27/50* (2013.01); *A61L 27/52* (2013.01); *A61L 27/58* (2013.01); *A61L 31/145* (2013.01); *A61L 31/148* (2013.01); *A61L 31/18* (2013.01); *A61K 2123/00* (2013.01)

(58) Field of Classification Search
  CPC ....... A61K 31/148; A61K 31/18; A61L 27/52; A61L 27/58; A61P 43/00; A61P 35/00; A61P 15/00
  See application file for complete search history.

(56) References Cited

U.S. PATENT DOCUMENTS

| | | |
|---|---|---|
| 3,872,856 A | 3/1975 | Clayton |
| 3,992,562 A | 11/1976 | Denzinger et al. |
| 4,002,173 A | 1/1977 | Manning et al. |
| 4,014,335 A | 3/1977 | Arnold |
| 4,193,813 A | 3/1980 | Chvapil |
| 4,207,893 A | 6/1980 | Michaels |
| 4,703,108 A | 10/1987 | Silver et al. |
| 4,714,074 A | 12/1987 | Rey et al. |
| 4,741,872 A | 5/1988 | DeLuca et al. |
| 4,815,449 A | 3/1989 | Horowitz |
| 4,826,945 A | 5/1989 | Cohn et al. |
| 4,938,763 A | 7/1990 | Dunn et al. |
| 4,970,298 A | 11/1990 | Silver et al. |
| 5,100,992 A | 3/1992 | Cohn et al. |
| 5,160,745 A | 11/1992 | De Luca et al. |
| 5,162,430 A | 11/1992 | Rhee et al. |
| 5,304,595 A | 4/1994 | Rhee et al. |
| 5,324,775 A | 6/1994 | Rhee et al. |
| 5,410,016 A | 4/1995 | Hubbell et al. |
| 5,499,994 A | 3/1996 | Tihon et al. |
| 5,514,379 A | 5/1996 | Weissleder et al. |
| 5,529,914 A | 6/1996 | Hubbell et al. |
| 5,543,441 A | 8/1996 | Rhee et al. |
| 5,550,187 A | 8/1996 | Rhee et al. |
| 5,565,215 A | 10/1996 | Gref et al. |
| 5,599,552 A | 2/1997 | Dunn et al. |
| 5,618,563 A | 4/1997 | Berde et al. |
| 5,629,008 A | 5/1997 | Lee |
| 5,733,316 A | 3/1998 | Tierney et al. |
| 5,752,974 A | 5/1998 | Rhee et al. |
| 5,759,583 A | 6/1998 | Iwamoto et al. |
| 5,767,284 A | 6/1998 | Sanchika et al. |
| 5,863,984 A | 1/1999 | Doillon et al. |
| 5,872,191 A | 2/1999 | Sanchika et al. |
| 5,874,500 A | 2/1999 | Rhee et al. |
| 5,900,245 A | 5/1999 | Sawhney et al. |
| 5,932,539 A | 8/1999 | Stupp et al. |
| 6,031,148 A | 2/2000 | Hayes et al. |
| 6,051,248 A | 4/2000 | Sawhney et al. |
| 6,060,534 A | 5/2000 | Ronan et al. |
| 6,063,061 A | 5/2000 | Wallace et al. |
| 6,083,524 A | 7/2000 | Sawhney et al. |
| 6,110,484 A | 8/2000 | Sierra |
| 6,121,341 A | 9/2000 | Sawhney et al. |
| 6,129,761 A | 10/2000 | Hubbell |
| 6,149,931 A | 11/2000 | Schwartz et al. |
| 6,152,943 A | 11/2000 | Sawhney |
| 6,165,201 A | 12/2000 | Sawhney et al. |
| 6,176,871 B1 | 1/2001 | Pathak et al. |
| 6,177,095 B1 | 1/2001 | Sawhney et al. |
| 6,177,514 B1 | 1/2001 | Pathak et al. |
| 6,179,862 B1 | 1/2001 | Sawhney |
| 6,201,065 B1 | 3/2001 | Pathak et al. |
| 6,206,930 B1 | 3/2001 | Burg et al. |
| 6,210,314 B1 | 4/2001 | Ein-Gal |
| 6,214,045 B1 | 4/2001 | Corbitt, Jr. et al. |
| 6,224,893 B1 | 5/2001 | Langer et al. |
| 6,268,405 B1 | 7/2001 | Yao et al. |
| 6,271,278 B1 | 8/2001 | Park et al. |
| 6,280,772 B1 | 8/2001 | Pinkus |
| 6,306,418 B1 | 10/2001 | Bley |
| 6,371,975 B2 | 4/2002 | Cruise et al. |
| 6,375,634 B1 | 4/2002 | Carroll |
| 6,379,373 B1 | 4/2002 | Sawhney et al. |
| 6,383,344 B1 | 5/2002 | Miller et al. |
| 6,387,977 B1 | 5/2002 | Sawhney et al. |
| 6,388,047 B1 | 5/2002 | Won et al. |
| 6,413,742 B1 | 7/2002 | Olsen et al. |
| 6,426,145 B1 | 7/2002 | Moroni |
| 6,436,424 B1 | 8/2002 | Vogel et al. |
| 6,475,477 B1 | 11/2002 | Kohn et al. |
| 6,479,079 B1 | 11/2002 | Pathak et al. |
| 6,509,031 B1 | 1/2003 | Miller et al. |
| 6,514,534 B1 | 2/2003 | Sawhney |
| 6,544,503 B1 | 4/2003 | Vanderhoff et al. |
| 6,545,097 B2 | 4/2003 | Pinchuk et al. |
| 6,566,406 B1 | 5/2003 | Pathak et al. |
| 6,592,859 B1 | 7/2003 | Bley |
| 6,596,471 B2 | 7/2003 | Pathak et al. |
| 6,599,448 B1 | 7/2003 | Ehrhard, Jr. et al. |
| 6,605,294 B2 | 8/2003 | Sawhney |
| 6,632,457 B1 | 10/2003 | Sawhney |
| 6,639,014 B2 | 10/2003 | Pathak et al. |
| 6,656,200 B2 | 12/2003 | Li et al. |
| 6,660,301 B1 | 12/2003 | Vogel et al. |
| 6,673,093 B1 | 1/2004 | Sawhney |
| 6,689,148 B2 | 2/2004 | Sawhney et al. |
| 6,703,047 B2 | 3/2004 | Sawhney et al. |
| 6,761,908 B1 | 7/2004 | Roreger |
| 6,818,018 B1 | 11/2004 | Sawhney |
| 6,862,470 B2 | 3/2005 | Burbank et al. |
| 6,875,841 B2 | 4/2005 | Sakanoue et al. |
| 6,887,974 B2 | 5/2005 | Pathak |
| 6,899,889 B1 | 5/2005 | Hnojewyj et al. |
| 6,913,744 B2 | 7/2005 | Gokcen |
| 6,923,986 B2 | 8/2005 | Pathak et al. |
| 6,958,212 B1 | 10/2005 | Hubbell et al. |
| 7,009,034 B2 | 3/2006 | Pathak et al. |
| 7,025,990 B2 | 4/2006 | Sawhney |
| 7,049,346 B1 | 5/2006 | Van Bladel et al. |
| 7,129,210 B2 | 10/2006 | Lowinger et al. |
| 7,211,651 B2 | 5/2007 | Pathak |
| 7,220,270 B2 | 5/2007 | Sawhney et al. |
| RE39,713 E | 7/2007 | Sawhney et al. |
| 7,238,364 B2 | 7/2007 | Sawhney et al. |
| 7,332,566 B2 | 2/2008 | Pathak et al. |
| 7,413,752 B2 | 8/2008 | Sawhney |
| 7,473,417 B2 | 1/2009 | Zeltinger et al. |
| 7,597,882 B2 | 10/2009 | Pathak et al. |
| 7,648,713 B2 | 1/2010 | Sawhney |
| 7,655,747 B2 | 2/2010 | Harris |
| 7,744,913 B2 | 6/2010 | Noyes |
| 7,776,063 B2 | 8/2010 | Sawhney et al. |
| 7,790,141 B2 | 9/2010 | Pathak et al. |

(56) References Cited

U.S. PATENT DOCUMENTS

| | | | |
|---|---|---|---|
| 7,914,541 | B2 | 3/2011 | Sawhney et al. |
| 7,964,217 | B2 | 6/2011 | Harris |
| 8,044,137 | B2 | 10/2011 | Khosravi et al. |
| 8,105,622 | B2 | 1/2012 | Sawhney |
| 8,257,723 | B2 | 9/2012 | Noyes |
| 8,383,161 | B2 | 2/2013 | Campbell et al. |
| 8,410,189 | B2 | 4/2013 | Carnahan et al. |
| 8,512,749 | B2 | 8/2013 | Sawhney et al. |
| 8,535,705 | B2 | 9/2013 | Pathak et al. |
| 8,642,085 | B2 | 2/2014 | Cassingham et al. |
| 8,685,367 | B2 | 4/2014 | Brandom et al. |
| 8,734,930 | B2 | 5/2014 | Bennett et al. |
| 8,795,709 | B2 | 8/2014 | Sawhney et al. |
| 8,802,146 | B2 | 8/2014 | Cassingham et al. |
| 8,846,022 | B2 | 9/2014 | Carnahan et al. |
| 8,852,646 | B2 * | 10/2014 | Campbell .......... A61K 51/1244 424/501 |
| 9,023,379 | B2 | 5/2015 | Pathak et al. |
| 9,186,422 | B2 | 11/2015 | Pathak et al. |
| 9,308,283 | B2 | 4/2016 | Campbell et al. |
| 9,393,344 | B2 | 7/2016 | Stockman et al. |
| 9,498,557 | B2 | 11/2016 | Pathak et al. |
| 9,669,117 | B2 | 6/2017 | Campbell et al. |
| 9,789,073 | B2 | 10/2017 | Pathak |
| 9,789,231 | B2 | 10/2017 | Goodrich |
| 9,878,066 | B2 | 1/2018 | Stockman et al. |
| 2003/0012734 | A1 | 1/2003 | Pathak et al. |
| 2003/0194389 | A1 | 10/2003 | Porter |
| 2004/0086479 | A1 | 5/2004 | Grinstaff et al. |
| 2004/0086548 | A1 | 5/2004 | St. John et al. |
| 2004/0131582 | A1 | 7/2004 | Grinstaff et al. |
| 2004/0133275 | A1 | 7/2004 | Mansmann |
| 2005/0036946 | A1 | 2/2005 | Pathak et al. |
| 2005/0080445 | A1 | 4/2005 | Sawhney et al. |
| 2006/0177481 | A1 | 8/2006 | Sawhney |
| 2006/0193899 | A1 | 8/2006 | Sawhney |
| 2007/0231366 | A1 | 10/2007 | Sawhney et al. |
| 2007/0264227 | A1 | 11/2007 | Lutolf et al. |
| 2008/0033471 | A1 | 2/2008 | Paz et al. |
| 2008/0114092 | A1 | 5/2008 | Sawhney |
| 2008/0187568 | A1 | 8/2008 | Sawhney |
| 2008/0220047 | A1 | 9/2008 | Sawhney et al. |
| 2008/0281388 | A1 | 11/2008 | Corbitt et al. |
| 2009/0011038 | A1 | 1/2009 | Seiler et al. |
| 2009/0053276 | A1 | 2/2009 | Richard |
| 2009/0117188 | A1 | 5/2009 | Gershkovich et al. |
| 2010/0104625 | A1 | 4/2010 | Putnam et al. |
| 2011/0286956 | A1 | 11/2011 | Zhao et al. |
| 2016/0271267 | A1 | 9/2016 | Lin et al. |
| 2017/0216487 | A1 | 8/2017 | Sawhney et al. |
| 2017/0266324 | A1 | 9/2017 | Campbell et al. |
| 2018/0044280 | A1 | 2/2018 | Zhu et al. |
| 2020/0277449 | A1 * | 9/2020 | De Cola ............ C08G 73/1067 |

FOREIGN PATENT DOCUMENTS

| | | |
|---|---|---|
| EP | 1996243 B1 | 4/2014 |
| EP | 2397164 B1 | 4/2015 |
| EP | 2247645 B1 | 12/2017 |
| WO | 98/12274 | 3/1998 |
| WO | 00/24387 | 10/1999 |
| WO | 99/59501 | 11/1999 |
| WO | 00/28919 | 5/2000 |
| WO | 00/45792 | 8/2000 |
| WO | 2001/085062 | 11/2001 |
| WO | 03/031388 | 4/2003 |
| WO | 2006/001009 | 1/2006 |
| WO | 2006/031358 | 3/2006 |
| WO | 2006/031388 | 3/2006 |
| WO | 2006/078770 | 7/2006 |
| WO | 2007/001926 | 1/2007 |
| WO | 2007/005249 | 1/2007 |
| WO | 2010/062783 | 6/2010 |

OTHER PUBLICATIONS

Bailey et al., "Synthesis of Polymerized Vesicles with Hydrolyzable Linkages", Macromolecules, 25:3-11 (1992).

Ball et al., "Silicone Implant to Prevent Visceral Damage During Adjuvant Radiotherapy for Retroperitoneal Sarcoma", The British Journal of Radiology, vol. 63:346-348 (1990).

Burnett et al., "The Use of a Pelvic Displacement Prosthesis to Exclude the Small Intestine From the Radiation Field Following Radical Hysterectomy", Gynecologic Oncology, vol. 79:438-443 (2000).

Cheng et al., "Collagen and Injectable Fillers", Otolaryngologic Clinics of North America, vol. 35(1):73-85 (Feb. 2002).

DeSalva et al., "NA22CL Skin Clearance in Humans and Its Relation to Skin Age", The Journal of Investigative Dermatology, vol. 45(5):315-318 (1965).

Dasmahapatra et al., "The Use of a Biodegradable Mesh to Prevent Radiation-Associated Small-Bowel Injury", Archives of Surgery, vol. 126:366-369 (Mar. 1991).

Galeska et al., "Controlled Release of Dexamethasone from PLGA Microspheres Embedded Within Polyacid-Containing PVA Hydrogels", AAPS Journal, 7(1):E231-E240 (Sep. 2, 2005).

Gander et al., "Crosslinked Poly(alkylene Oxides) for the Preparation of Controlled Release Micromatrices", Journal of Controlled Release, 5:271-283 (1988).

Gayet et al, "High Water Content BSA-PEG Hydrogel for Controlled Release Device: Evaluation of the Drug Release Properties", Journal of Controlled Release, 38:177-184 (1996).

Hatiboglu et al., "Application Technique: Placement of a Prostate-Rectum Spacer in Men Undergoing Prostate Radiation Therapy", BJU International, 1-6 Pages (May 10, 2012).

Horak et al., "Hydrogels in Endovascular Embolization. III. Radiopaque Spherical Particles, Their Preparation and Properties", Biomaterials, vol. 8:142-145 (Mar. 1987).

Hoffman et al., "Morbidity After Intraperitoneal Insertion of Saline-Filled Tissue Expanders for Small Bowel Exclusion From Radiotherapy Treatment Fields: A Prospective Four Years Experience With 34 Patients", The American Surgeon, vol. 60(7):473-483 (Jul. 1994).

Hyon, "Biodegradable Poly(Lactic Acid) Microsphers for Drug Delivery Systems", Yonsei Medical Journal, 41(6):720-734 (2000).

Jayakrishnan et al., "Hydrogel Microspheres from Crosslinked Poly(methyl methacrylate): Synthesis and Biocompatibility Studies", Bull Mater Sci, vol. 12(1):17-25 (Mar. 1989).

Kimura et al., "Injectable Microspheres with Controlled Drug Release for Glaucoma Filtering Surgery", Investigative Ophthalmology & Visual Science, 33(12): 3436-3441 (Nov. 1992).

Lasic et al., "Sterically Stabilized Liposomes*: A Hypothesis on the Molecular Origin of the Extended Circulation Times", Biochimica et Biophysica Acta, 1070:187-192 (1991).

Lin et al., "Hyaluronic Acid-Filled Mammary Implants: An Experimental Study", Plastic and Reconstructive Surgery, vol. 94(2):306-315 (1994).

Lipschitz et al., "Subcutaneous Fluid Administration in Elderly Subjects: Validation of an Under-Used Technique", JAGS vol. 36(1):6-9 (Jan. 1991).

Mathiowitz et al., "Polyanhydride Microspheres as Drug Carriers I. Hot-Melt Microencapsulation", Journal of Controlled Release 5:13-22 (1987).

Mawad, et al., "Synthesis and Characterization of Radiopaque Iodine-containing degradable PVA Hydrogels", Biomacromoloecules, 9:263-268 (2008).

Mayhew et al., "Characterization of Liposomes Prepared Using a Microemulsifier", Biochimica et Biophysica Acta, 775:169-174 (1984).

Mettler et al., "Prospective Clinical Trial of SprayGel as a Barrier to Adhesion Formation: An Interim Analysis", The Journal of the American Association of Gynecologic Laparoscopists, 10(3):339-344 (Aug. 2003).

Nihant et al., "Polylactide Microparticles Prepared by Double Emulsion-Evaporation", Journal of Colloid & Interface Science, 173:55-65 (1995).

(56) References Cited

OTHER PUBLICATIONS

Noyes et al., "Human Collagen Injections to Reduce Rectal Dose During Radiotherapy", International Journal of Radiation Oncology Biology Physics, vol. 82(5):1918-1922 (2012).

Onik, "Image-Guided Prostate Cryosurgery: State of the Art", Cancer Control, vol. 8(6):522-531 (Dec. 2001).

Park, "Enzyme-Digestible Swelling Hydrogels as Platforms for Long-Term Oral Drug Delivery: Synthesis and Characterization", Biomaterials, 9:435-441 (1988).

Pinkawa, Spacer Application for Prostate Cancer Radiation Therapy, Future Oncology, vol. 10(5):851-864 (2014).

Prada et al., "Transperineal Injection of Hyaluronic Acid in Anterior Perirectal Fat to Decrease Rectal Toxicity from Radiation Delivered with Intensity Modulated Brachytherapy or Ebrt for Prostate Cancer Patients", International Journal of Radiation Oncology Biology Physics, 69(1):95-102 (2007).

Reddy et al., "Polyurethane Microspheres as Drug Carriers", Macromolecular Reports, A32(suppls. 5& 6):789-799 (1995).

Sasson et al., "Hypodermoclysis an Alternative Infusion Technique", American Family Physician, vol. 64(9):1575-1578 (Nov. 1, 2001).

Spearman et al., "The Site of Deposition and Rate of Clearance of Saline After Subcutaneous Injection Into the Mouse Tail", The Journal of Investigative Dermatology, vol. 46(3):251-253 (1966).

Sugarbaker et al., "Intrapelvic Prosthesis to Prevent Injury of the Small Intestine With High Dosage Pelvic Irradiation", Surgery, Gynecology & Obstetrics, vol. 157:269-271 (Sep. 1983).

Tabata et al., "Controlled Delivery Systems for Proteins Using Polyanhydride Microspheres", Pharmaceutical Research, 10(4):487-496 (1993).

Torchilin et al., "Liposome-Polymer Systems. Introduction of Liposomes into a Polymer Gel and Preparation of the Polymer Gel Inside a Liposome," Polymer Science U.S.S.R., 30(10):2307-2312 (1988).

Trachtenberg et al., "Prostate Cancer: 11. Alternative Approaches and the Future of Treatment", Canadian Medical Association, vol. 160(4):528-534 (1999).

Supplementary European Search Report from corresponding PCT Application No. PCT/US2010/060474, 10 pages, dated Jul. 15, 2013.

Devereux et al., "Protection From Radiation Enteritis by an Absorbable Polyglycolic Acid Mesh Sling", Surgery, 123-129, (Jun. 6, 1986).

Duranti et al., "Injectable Hyaluronic Acid Gel for Soft Tissue Augmentation", Dermatol Surgery, vol. 24:1317-1325 (1998).

\* cited by examiner

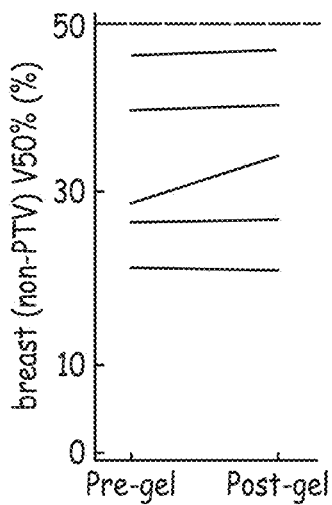 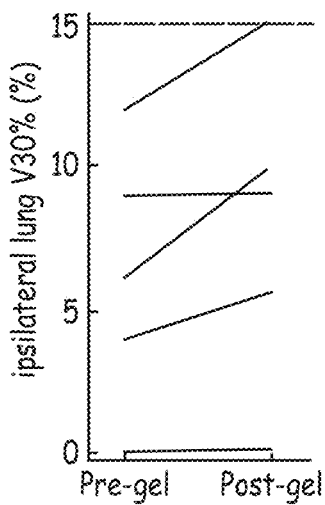 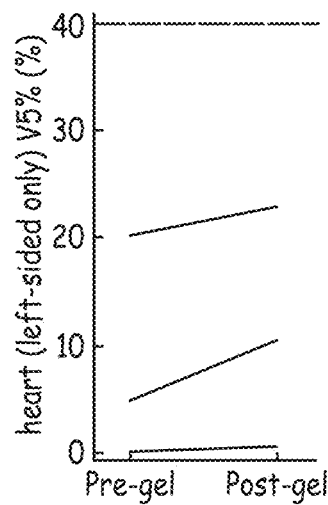
FIG. 6A　　　FIG. 6B　　　FIG. 6C
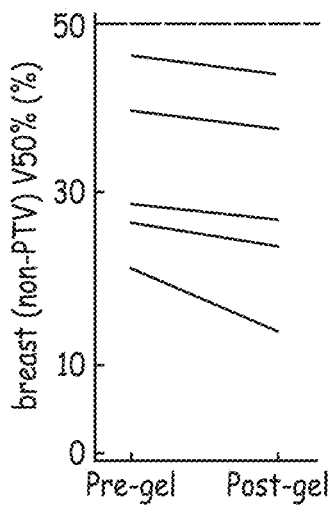 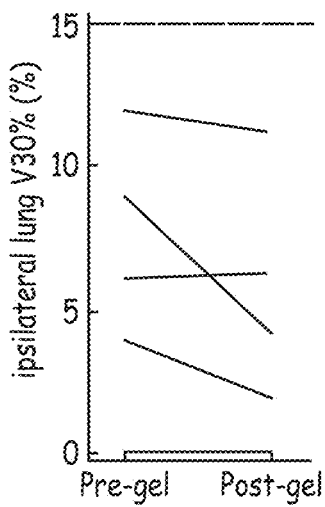 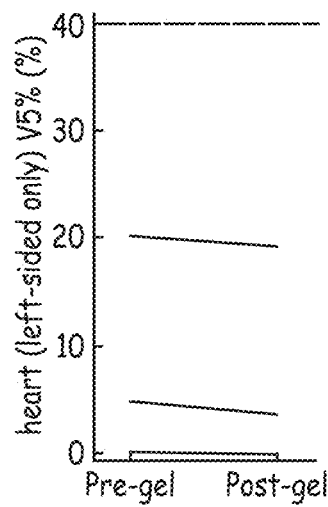
FIG. 7A　　　FIG. 7B　　　FIG. 7C

ECHOLUCENT IMPLANT COMPOSITIONS AND METHODS

CROSS REFERENCE TO RELATED APPLICATIONS

This application is a continuation of U.S. patent application Ser. No. 16/296,795, filed Mar. 8, 2019 which is a continuation of U.S. patent application Ser. No. 15/613,555, filed Jun. 5, 2017 which is a continuation of U.S. patent application Ser. No. 15/066,707, filed Mar. 10, 2016 which is a continuation of U.S. patent application Ser. No. 14/465,202 filed Aug. 21, 2014 which is a divisional of U.S. patent application Ser. No. 13/750,570, filed Jan. 25, 2013 which is a divisional of U.S. patent application Ser. No. 12/968,527, filed Dec. 15, 2010, which claims the benefit of U.S. Provisional Application No. 61/286,450, filed Dec. 15, 2009, each of which are hereby incorporated by reference herein in their entirety.

TECHNICAL FIELD

The technical field, in general, relates to stabilizing and visualizing tissue gaps left by surgical removal of cancerous tissues; certain embodiments include polymeric microparticles with attached radioopaque markers.

BACKGROUND

According to the American Cancer Society, in 2009 it is estimated there will be more than 192,000 and 62,000 new cases of invasive and in situ breast cancer, respectively, with more with over 40,000 deaths in the United States alone. Once detected, most breast cancers, including ductal carcinoma in situ (DCIS), are removed surgically either by a modified radical mastectomy, or via lumpectomy. Following lumpectomy, patents are then typically treated with either chemotherapy followed by 5-7 weeks of whole breast external beam radiation therapy (EBRT), or by 5-7 days of accelerated partial breast irradiation (APBI) followed by either chemotherapy or no further treatment.

SUMMARY

Implants are described herein that conformally fill surgical sites. Conformal filling of the sites with a radioopaque material provides for later identification and monitoring of the site and its tissue margins. Good visualization allows for careful post-operative follow-up of cancer patients who have had cancerous tissue removed. In the first place, filling substantially all of the site provides a bulky mass that resists permanent deformation and migration of the margins. Further, the margins can be visualized because the site is substantially full and the implant is thus coterminous with the tissue margins.

One embodiment of an implant involves filling a site with flowable precursors that set-up to make a hydrogel implant that provides for ready visualization of margins of the implant site. The implant immobilizes and may adhere to the tissue edges, so that the edges can be followed and subsequently treated. A process for making the implant involves reacting precursors with each other that form the implant when they react with each other. A crosslinked hydrogel can be formed in-situ that supports tissue around a lumpectomy site to stabilize the tissue at the margins of the lumpectomy so the margins can be precisely targeted by subsequent treatments, for instance, radiation or ablation.

Another embodiment of the invention provides filling the site with small particles that are small, pliable, and slippery so that they flow easily into the site and its irregularities, pack closely, and provide good visualization of the margins. Radioopaque agents may be included with the implants, either covalently attached or mixed within the materials.

A conformal filling approach is a considerable improvement over the use of clips, which provide poor resolution of the site's margins. Conformal filling also improves over a do-nothing approach which is also a conventional practice that allows a void to remain at the surgical site to be filled with a seroma. Seromas can be symptomatic, often requiring drainage, and are known to change size following surgery, preventing targeting for partial breast irradiation. The implants may be formulated to be stable until no longer needed, and then biodegrade. The implants may also be used with or without radioopaque agents. An in situ formed hydrogel can seal tissue margins to reduce seroma formation. Further, the use of hydrogel as a continuous phase or as a particulate form may result in improved cosmesis since the hydrogel fills the cavity and prevents its deformation.

BRIEF DESCRIPTION OF THE DRAWINGS

FIG. 6A is a plot of breast (non-PTV) V50% for a set of treatment plans with 25 mm margins. Each line corresponds to one pair of pre/post-hydrogel plans. The breast (non-PTV) V50% increased due to hydrogel placement in four of five cases; however, the increases were modest compared with the volume constraint of 50%.

FIG. 6B is a plot of the treatment plans of FIG. 6A and shows how ipsilateral lung V30% also increased in four of five cases; increases were more sizeable relative to the volume constraint of 15%.

FIG. 6C is a plot of the treatment plans of FIG. 7A and shows how, for all left sided lumpectomies, hydrogel increased the heart V5%, but the volumes remained well under the 40% constraint.

FIG. 7A is a plot that describes treatment plans with 15 mm margins. The breast (non-PTV) V50% decreased in all five cases.

FIG. 7B is a plot of the treatment plans of FIG. 7A and shows how ipsilateral lung V30% also decreased in four of five cases.

FIG. 7C is a plot of the treatment plans of FIG. 7A and shows how, for all left-sided lumpectomies, the heart V5% also showed small decreases.

DETAILED DESCRIPTION

Figure 1A:
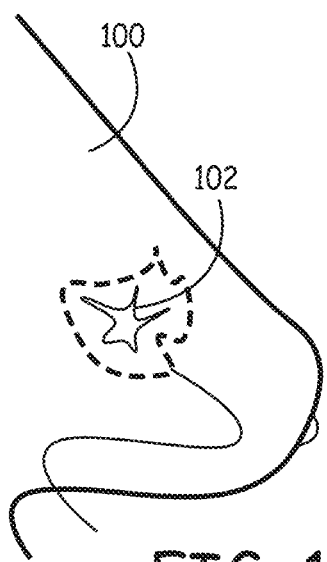
FIG. 1A is an illustration of the prior art for removing a tumor from a tissue.
Figure 1B:
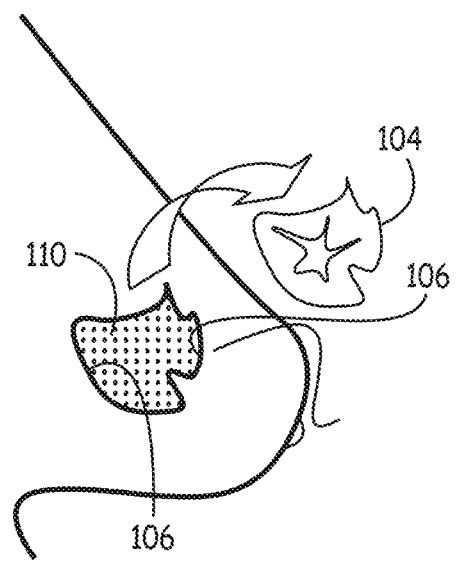
FIG. 1B is an illustration of the prior art for removing a tumor from a tissue.

Tissues around an iatrogenic (medically-created) site can be stabilized by conformal implants that are placed in the site. The implants' conforming to the sites provides for accurate follow-on treatments. After removal of malignant tissue material, for instance, further treatment of tissue around the removed material is often desired, for instance, by radiation of the margins of the site or tissue-ablative techniques. It is difficult to target the margins with precision, however, since the margins are hard to visualize and shift size and shape over the course of time. FIGS. 1A and 1B depict breast tissue 100 having tumor 102. Surgery involves removal of tumor 102 and surrounding tissue. The removed tissue material 104 has a shape and a volume. Removal of material 104 creates iatrogenic site 110 (also referred to as a cavity) also having a shape and a volume that are defined by surface 116, which is the tissue margins of the iatrogenic site. Site 110 is clearly bounded, with those boundaries being surfaces. In the case of a site that is not entirely within the body, the shape and volume of the site can nonetheless be defined with reasonable accuracy by referring the shape and volume of the removed material.

Conventionally, the cavity is imaged before radiation. In cases where there is no seroma, the cavity is hard to even identify. While clips for imaging are helpful, these provide only individual points that do not define the cavity edges. Even when a seroma is present, the cavity changes shape over the several weeks of radiation. The target thus changes from the initial plan, potentially moving cancer cells out of the radiation, or healthy tissue into it. As a result, it is sometimes necessary to simply irradiate the whole breast.

Figure 2A:
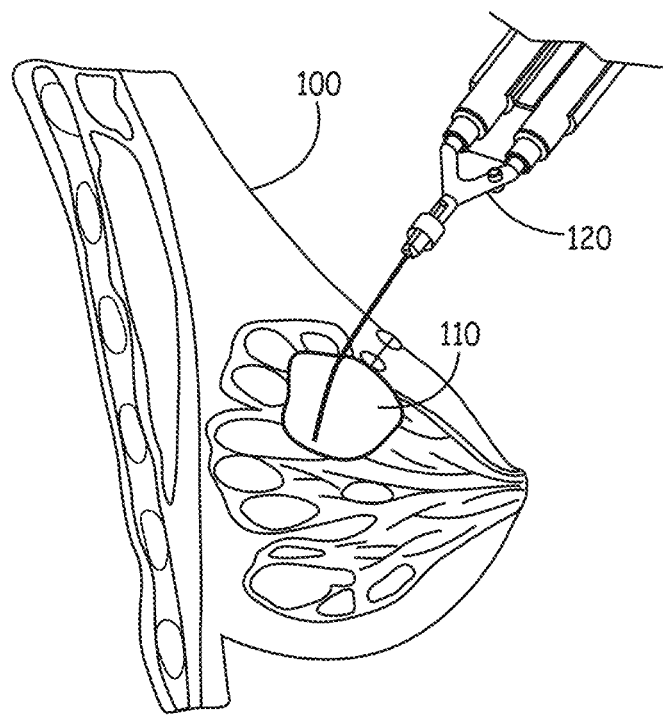
FIG. 2A illustrates placement of matrix precursors in an iatrogenic site using a dual-barreled applicator.
Figure 2B:
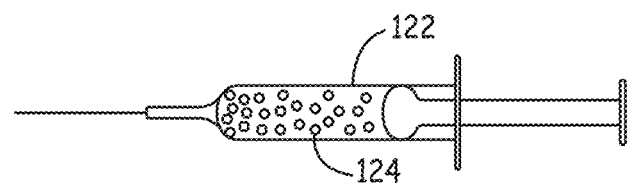
FIG. 2B depicts an alternative applicator for placing a plurality of particles into the site of FIG. 2A.

One embodiment of the invention solves these problems by providing a matrix that conformally fills the site where it is placed. Experiments have shown that it is possible to have good indirect visibility and true conformal filling with this approach, and that such a hydrogel may additionally and/or alternatively be used as a fiducial marker. The hydrogel can be degradable over a span of time that provides stability during a medically required time but dissolution afterwards. The stability of the hydrogel provides for stability of the site, which might otherwise change shape. FIG. 2A schematically depicts filling site 110 using a double-barreled applicator that supplies precursors that form the hydrogel inside site 110. FIG. 2B depicts an alternative syringe applicator 122 loaded with a plurality of particles 124 that are placed in the site to form a matrix. Catheters and other applicators may also be used.

Figure 3A:
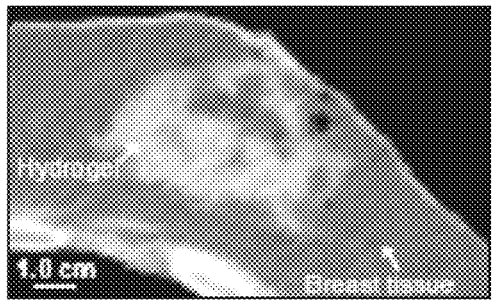
FIG. 3A is an image of a hydrogel placed in an iatrogenic site with clear definition of the lumpectomy cavity on kilovoltage CT.
Figure 3B:
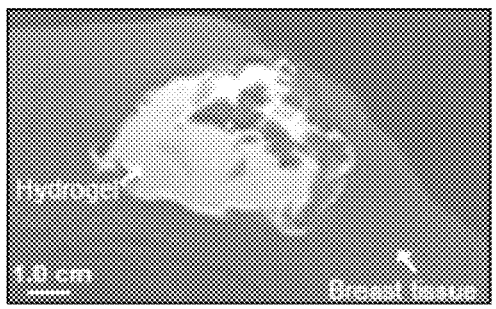
FIG. 3B is a T2-weighted MRI image of the site of FIG. 3A.
Figure 3C:
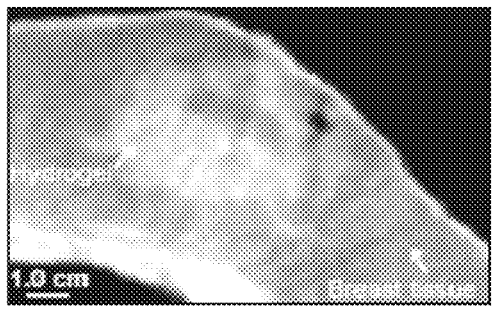
FIG. 3C is a kilovoltage cone-beam CT image of the site of FIG. 3A.
Figure 3D:
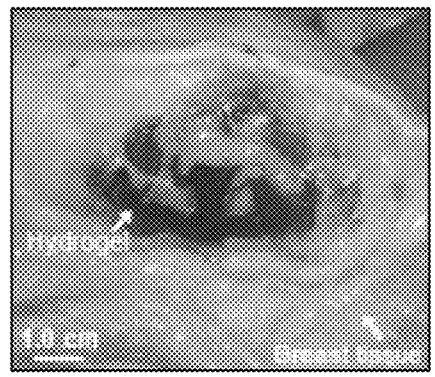
FIG. 3D is a photomicrograph image of a gross axial section (hydrogel is dyed blue) of the site of FIG. 3A.
Figure 3E:
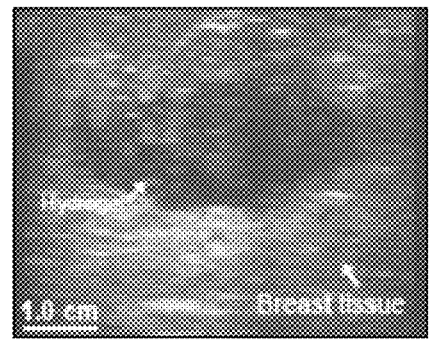
FIG. 3E is an axial ultrasound image of the site of FIG. 3A.
Figure 4A:
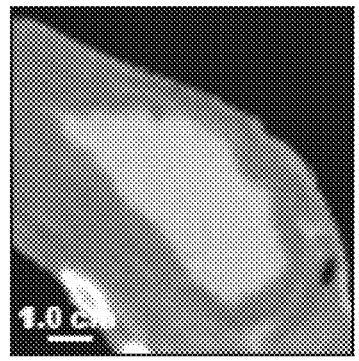
FIG. 4A is a CT image of a hydrogel iatrogenic site treatments of a 63 cc lumpectomy that was filled with an equal volume of hydrogel.
Figure 4B:
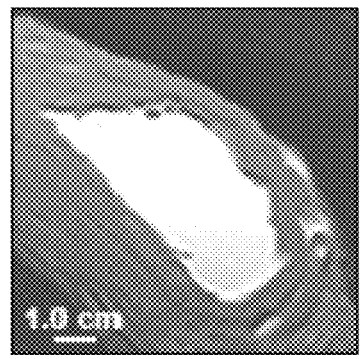
FIG. 4B is an MRI image of the site of FIG. 4A.
Figure 4C:
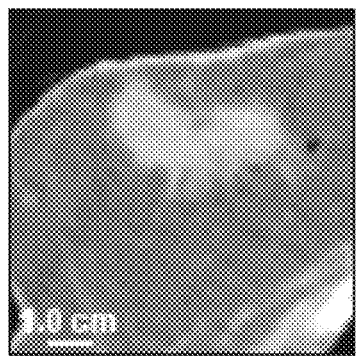
FIG. 4C is a CT image of a 31 cc lumpectomy site that was partially filled with 18 cc of hydrogel.
Figure 4D:
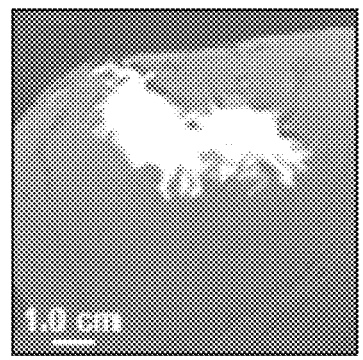
FIG. 4D is an MRI image of the site of FIG. 4C.
Figure 4E:
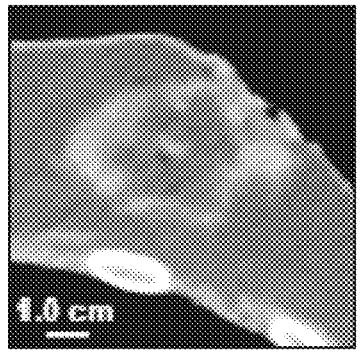
FIG. 4E is a 33 cc lumpectomy cavity site that was sutured closed (the superior and inferior cavity walls were apposed) and then injected with 18 cc of hydrogel; the hydrogel marks the edges of the cavity, outlining the apposed tissue.
Figure 4F:
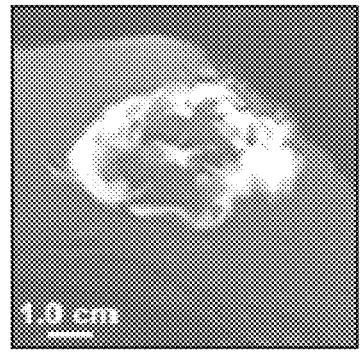
FIG. 4F is an MRI image of the site of FIG. 4E.

Example 1 describes a matrix that is applied to an iatrogenic site as a liquid mixture of two precursors that covalently crosslink with each other to form a hydrogel. The hydrogel revealed fine details of the lumpectomy cavity shape and size, with good correspondence between CT, MRI, cone-beam CT, and gross pathologic sections. Importantly, the lumpectomy site was well defined for partially filled cavities and even for cavities that were sutured closed (which, historically, have been very difficult to accurately define). In all cases, gross dissection showed that hydrogel coated the entire cavity surface, i.e., was truly conformal to the tissue margins of the site. FIG. 3 shows that the hydrogel clearly defined the site: kilovoltage CT in FIG. 3A; T2-weighted MRI in FIG. 3B; kilovoltage cone-beam CT in FIG. 3C; gross axial section (hydrogel is dyed blue) in FIG. 3D, and axial ultrasound in FIG. 3E. FIG. 4 shows good definition with CT and MRI: a 63 cc volume defect site was filled with an equal volume of hydrogel (FIG. 4A (CT) and FIG. 4B (MRI)). In FIG. 4C (CT) and FIG. 4D (MRI), a 31 cc lumpectomy was partially filled with 18 cc of hydrogel, and shows that the cavity is still well defined. In FIG. 4E (CT) and FIG. 4F (MRI) a 33 cc lumpectomy cavity was sutured closed and then injected with 18 cc of hydrogel; the hydrogel marks the edges of the cavity, outlining the apposed tissue.

Example 2 describes a series of radiation plans for the treated sites, and compares plans for hydrogel-filled versus not-filled sites. Radiation plans are routinely made, and consider how much radiation to apply to a site in light of various considerations such as the desired dose, treatment regimen, and radiation limits for nearby healthy tissues. It is contrary to conventional wisdom to expand iatrogenic sites because it is well known that increased target size can increase radiation doses to nearby, normal tissues.

Figures 5A, 5B:
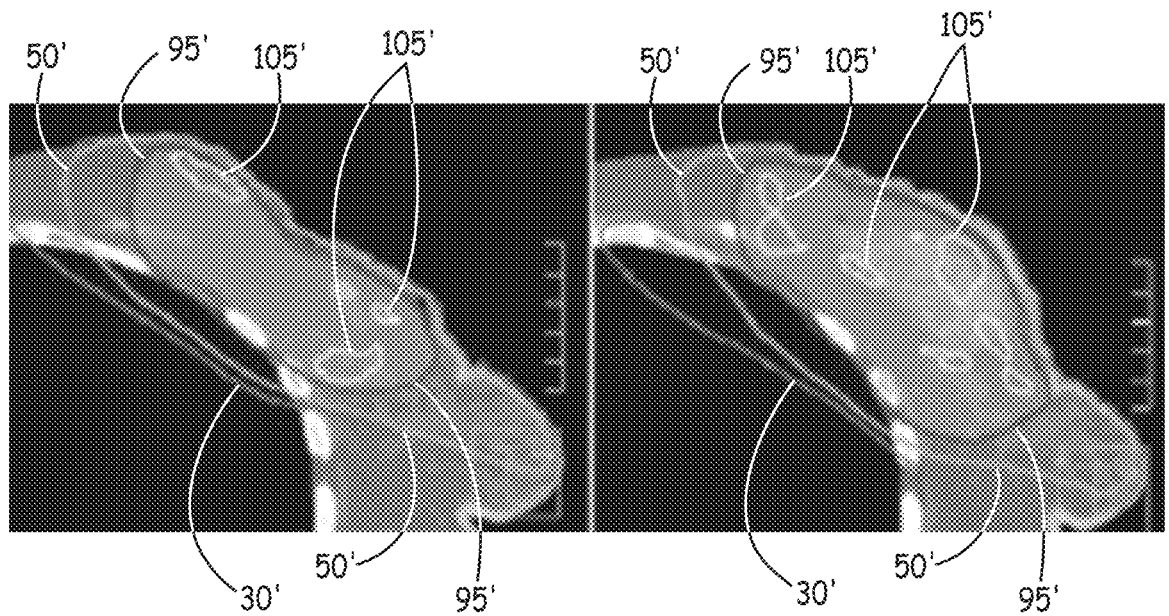
FIG. 5A provides details of five-field, partial-breast radiation treatment plans generated before a hydrogel was injected into lumpectomy cavities. Axial sections are shown. 105%, 95%, 50%, and 30% isodose contours are shown in lines 105', 95', 50', and 30', respectively.
FIG. 5B is a radiation treatment plan generated after the hydrogel injection of FIG. 5A.
Figure 5C:
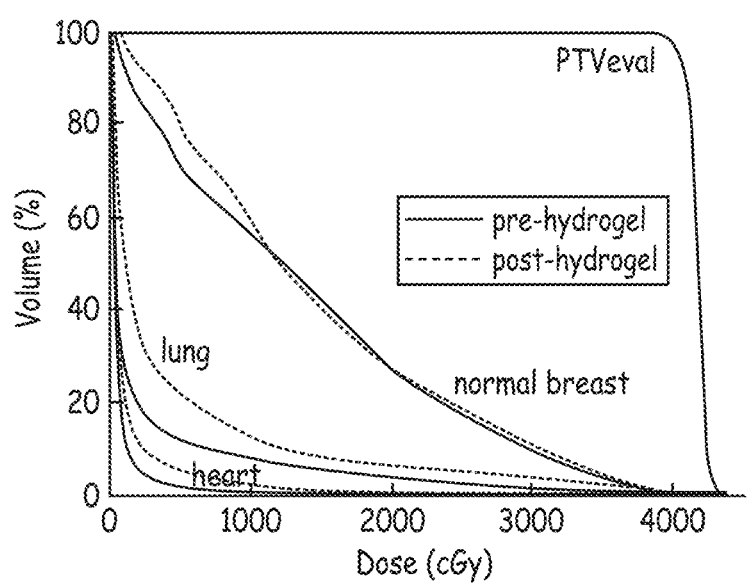
FIG. 5C is a DVH that shows only slightly higher radiation doses to the normal breast tissue, ipsilateral lung, and heart in the posthydrogel plan (dashed lines).

In fact, this undesirable effect was observed with the particular hydrogel that was tested, as illustrated in FIGS. 5 and 6 (see details in Example 2). FIG. 6 shows five-field, partial-breast radiation treatment plans generated both before and after the hydrogel was injected into the cavities. Axial sections (prehydrogel in FIG. 5A and post-hydrogel in FIG. 5B) are shown. 105%, 95%, 50%, and 30% isodose contours are shown in 105', 95', 50', 30', respectively. The evaluation-PTV is shaded and lies substantially in the 95' area. The DVH (FIG. 5C) shows slightly higher radiation doses to the normal breast tissue, ipsilateral lung, and heart in the posthydrogel plan (dashed lines). Evaluation-PTV coverage is similar, although the post-hydrogel plan shows slightly increased inhomogeneity. Similarly, FIG. 6 shows that, when using standard treatment expansion (25 mm), the hydrogel implant tends to increase normal tissues doses. Each line corresponds to one pair of pre/post-hydrogel plans. The breast (non-PTV) V50% increased due to hydrogel placement in four of five cases; however, the increases were modest compared with the volume constraint of 50% (FIG. 6A). Ipsilateral lung V30% also increased in four of five cases; increases were more sizeable relative to the volume constraint of 15% (FIG. 6B). For the left sided lumpectomies, hydrogel increased the heart V5%, but the volumes remained well under the 40% constraint (FIG. 6C).

Conventional treatment expansions of 25 mm beyond the PTV are utilized, in part, because if poor visualization of the cavity margins during dose planning. If the hydrogel was effective at delineating the cavity margins, then treatment localization uncertainty decreased, and a treatment expansion of 15 mm beyond the PTV may well be feasible. With a treatment expansion of 15 mm radiation exposure of healthy surrounding tissues was reduced compared to conventional treatments. FIG. 7 (see Example 2) details this effect. The breast (non-PTV) V50% decreased in all five cases (FIG. 7A). Ipsilateral lung V30% also decreased in four of five cases (FIG. 7B). For the left-sided lumpectomies, the heart V5% also showed small decreases (FIG. 7C). Consideration of the superior visualization aspects of the implant points to methods involving use of a hydrogel as an implant at a iatrogenic site with reduced treatment expansions, e.g., expansions of less than about 25 mm, or between about 2 and about 25 mm; artisans will immediately appreciate that all the ranges and values within the explicitly stated ranges are contemplated, e.g., less than about 20 mm, or from about 5 mm to less than about 25 mm.

Hydrogels and Hydrogel Precursors

Accordingly, embodiments are provided herein for making implant materials. Such materials include matrices with a porosity of more than about 20% v/v; artisans will immediately appreciate that all the ranges and values within the explicitly stated range is contemplated. Hydrogels are an embodiment of such an implant. Hydrogels are materials that do not dissolve in water and retain a significant fraction (more than 20%) of water within their structure. In fact, water contents in excess of 90% are often known. Hydrogels are often formed by crosslinking water soluble molecules to form networks of essentially infinite molecular weight. Hydrogels with high water contents are typically soft, pliable materials. A hydrogel that has been dried is referred to herein as a dehydrated hydrogel if it will return to a hydrogel state upon exposure to water; this hydrogel would expand in volume if it were exposed to an excess of water and not constrained. The term desiccated refers to a hydrogel essentially having no fluids, bearing in mind that some trace amounts of water may nonetheless be present.

Hydrogels may be formed from natural, synthetic, or biosynthetic polymers. Natural polymers may include glycosminoglycans, polysaccharides, and proteins. Some examples of glycosaminoglycans include dermatan sulfate, hyaluronic acid, the chondroitin sulfates, chitin, heparin, keratan sulfate, keratosulfate, and derivatives thereof. In general, the glycosaminoglycans are extracted from a natural source and purified and derivatized. However, they also may be synthetically produced or synthesized by modified microorganisms such as bacteria. These materials may be modified synthetically from a naturally soluble state to a partially soluble or water swellable or hydrogel state. This modification may be accomplished by various well-known techniques, such as by conjugation or replacement of ionizable or hydrogen bondable functional groups such as carboxyl and/or hydroxyl or amine groups with other more hydrophobic groups.

For example, carboxyl groups on hyaluronic acid may be esterified by alcohols to decrease the solubility of the hyaluronic acid. Such processes are used by various manufacturers of hyaluronic acid products (such as Genzyme Corp., Cambridge, Mass.) to create hyaluronic acid based sheets, fibers, and fabrics that form hydrogels. Other natural polysaccharides, such as carboxymethyl cellulose or oxidized regenerated cellulose, natural gum, agar, agrose, sodium alginate, carrageenan, fucoidan, furcellaran, laminaran, hypnea, eucheuma, gum arabic, gum ghatti, gum karaya, gum tragacanth, locust beam gum, arbinoglactan, pectin, amylopectin, gelatin, hydrophilic colloids such as carboxymethyl cellulose gum or alginate gum cross-linked with a polyol such as propylene glycol, and the like, also form hydrogels upon contact with aqueous surroundings.

Synthetic hydrogels may be biostable or biodegradable or biodegradable. Examples of bio stable hydrophilic polymeric materials are poly(hydroxyalkyl methacrylate), poly (electrolyte complexes), poly(vinylacetate) cross-linked with hydrolysable or otherwise degradable bonds, and water-swellable N-vinyl lactams. Other hydrogels include hydrophilic hydrogels known as CARBOPOL®, an acidic carboxy polymer (Carbomer resins are high molecular weight, allylpentaerythritol-crosslinked, acrylic acid-based polymers, modified with C10-C30 alkyl acrylates), polyacrylamides, polyacrylic acid, starch graft copolymers, acrylate polymer, ester cross-linked polyglucan. Such hydrogels are described, for example, in U.S. Pat. No. 3,640,741 to Etes, U.S. Pat. No. 3,865,108 to Hartop, U.S. Pat. No. 3,992,562 to Denzinger et al., U.S. Pat. No. 4,002,173 to Manning et al., U.S. Pat. No. 4,014,335 to Arnold and U.S. Pat. No. 4,207,893 to Michaels, all of which are incorporated herein by reference, with the present specification controlling in case of conflict.

Hydrogels may be made from precursors. The precursors are not hydrogels but are covalently crosslinked with each other to form a hydrogel and are thereby part of the hydrogel. Crosslinks can be formed by covalent or ionic bonds, by hydrophobic association of precursor molecule segments, or by crystallization of precursor molecule segments. The precursors can be triggered to react to form a crosslinked hydrogel. The precursors can be polymerizable and include crosslinkers that are often, but not always, polymerizable precursors. Polymerizable precursors are thus precursors that have functional groups that react with each other to form polymers made of repeating units. Precursors may be polymers.

Some precursors thus react by chain-growth polymerization, also referred to as addition polymerization, and involve the linking together of monomers incorporating double or triple chemical bonds. These unsaturated monomers have extra internal bonds which are able to break and link up with other monomers to form the repeating chain. Monomers are polymerizable molecules with at least one group that reacts with other groups to form a polymer. A macromonomer (or macromer) is a polymer or oligomer that has at least one reactive group, often at the end, which enables it to act as a monomer; each macromonomer molecule is attached to the polymer by reaction the reactive group. Thus macromonomers with two or more monomers or other functional groups tend to form covalent crosslinks. Addition polymerization is involved in the manufacture of, e.g., polypropylene or polyvinyl chloride. One type of addition polymerization is living polymerization.

Some precursors thus react by condensation polymerization that occurs when monomers bond together through condensation reactions. Typically these reactions can be achieved through reacting molecules incorporating alcohol, amine or carboxylic acid (or other carboxyl derivative) functional groups. When an amine reacts with a carboxylic acid an amide or peptide bond is formed, with the release of water. Some condensation reactions follow a nucleophilic acyl substitution, e.g., as in U.S. Pat. No. 6,958,212, which is hereby incorporated by reference herein in its entirety to the extent it does not contradict what is explicitly disclosed herein.

Some precursors react by a chain growth mechanism. Chain growth polymers are defined as polymers formed by the reaction of monomers or macromonomers with a reactive center. A reactive center is a particular location within a chemical compound that is the initiator of a reaction in which the chemical is involved. In chain-growth polymer chemistry, this is also the point of propagation for a growing chain. The reactive center is commonly radical, anionic, or cationic in nature, but can also take other forms. Chain growth systems include free radical polymerization, which involves a process of initiation, propagation and termination. Initiation is the creation of free radicals necessary for propagation, as created from radical initiators, e.g., organic peroxide molecules. Termination occurs when a radical reacts in a way that prevents further propagation. The most common method of termination is by coupling where two radical species react with each other forming a single molecule.

Some precursors react by a step growth mechanism, and are polymers formed by the stepwise reaction between functional groups of monomers. Most step growth polymers are also classified as condensation polymers, but not all step growth polymers release condensates.

Monomers may be polymers or small molecules. A polymer is a high molecular weight molecule formed by combining many smaller molecules (monomers) in a regular pattern. Oligomers are polymers having less than about 20 monomeric repeat units. A small molecule generally refers to a molecule that is less than about 2000 Daltons.

The precursors may thus be small molecules, such as acrylic acid or vinyl caprolactam, larger molecules containing polymerizable groups, such as acrylate-capped polyethylene glycol (PEG-diacrylate), or other polymers containing ethylenically-unsaturated groups, such as those of U.S. Pat. No. 4,938,763 to Dunn et al, U.S. Pat. Nos. 5,100,992 and 4,826,945 to Cohn et al, or U.S. Pat. Nos. 4,741,872 and 5,160,745 to DeLuca et al., each of which is hereby incorporated by reference herein in its entirety to the extent it does not contradict what is explicitly disclosed herein.

To form covalently crosslinked hydrogels, the precursors must be crosslinked together. In general, polymeric precursors will form polymers that will be joined to other polymeric precursors at two or more points, with each point being a linkage to the same or different polymers. Precursors with at least two reactive groups can serve as crosslinkers since each reactive group can participate in the formation of a different growing polymer chain. In the case of functional groups without a reactive center, among others, crosslinking requires three or more such functional groups on at least one of the precursor types. For instance, many electrophilic-nucleophilic reactions consume the electrophilic and nucleophilic functional groups so that a third functional group is needed for the precursor to form a crosslink. Such precursors thus may have three or more functional groups and may be crosslinked by precursors with two or more functional groups. A crosslinked molecule may be crosslinked via an ionic or covalent bond, a physical force, or other attraction. A covalent crosslink, however, will typically offer stability and predictability in reactant product architecture.

In some embodiments, each precursor is multifunctional, meaning that it comprises two or more electrophilic or nucleophilic functional groups, such that a nucleophilic functional group on one precursor may react with an electrophilic functional group on another precursor to form a covalent bond. At least one of the precursors comprises more than two functional groups, so that, as a result of electrophilic-nucleophilic reactions, the precursors combine to form crosslinked polymeric products.

The precursors may have biologically inert and hydrophilic portions, e.g., a core. In the case of a branched polymer, a core refers to a contiguous portion of a molecule joined to arms that extend from the core, with the arms having a functional group, which is often at the terminus of the branch. The hydrophilic precursor or precursor portion preferably has a solubility of at least 1 g/100 mL in an aqueous solution. A hydrophilic portion may be, for instance, a polyether, for example, polyalkylene oxides such as polyethylene glycol (PEG), polyethylene oxide (PEO), polyethylene oxide-co-polypropylene oxide (PPO), co-polyethylene oxide block or random copolymers, and polyvinyl alcohol (PVA), poly (vinyl pyrrolidinone) (PVP), poly (amino acids, dextran, or a protein. The precursors may have a polyalkylene glycol portion and may be polyethylene glycol based, with at least about 80% or 90% by weight of the polymer comprising polyethylene oxide repeats. The polyethers and more particularly poly (oxyalkylenes) or poly (ethylene glycol) or polyethylene glycol are generally hydrophilic.

A precursor may also be a macromolecule (or macromer), which is a molecule having a molecular weight in the range of a thousand to many millions. In some embodiments, however, at least one of the precursors is a small molecule of about 1000 Da or less. The macromolecule, when reacted in combination with a small molecule of about 1000 Da or less, is preferably at least five to fifty times greater in molecular weight than the small molecule and is preferably less than about 60,000 Da; artisans will immediately appreciate that all the ranges and values within the explicitly stated ranges are contemplated. A more preferred range is a macromolecule that is about seven to about thirty times greater in molecular weight than the crosslinker and a most preferred range is about ten to twenty times difference in weight. Further, a macromolecular molecular weight of 5,000 to 50,000 is useful, as is a molecular weight of 7,000 to 40,000 or a molecular weight of 10,000 to 20,000.

Certain macromeric precursors are the crosslinkable, biodegradable, water-soluble macromers described in U.S. Pat. No. 5,410,016 to Hubbell et al, entitled "Photopolymerizable Biogradable Hydrogels as Tissue contacting Materials and Controlled-Release Carriers," which is hereby incorporated herein by reference in its entirety to the extent it does not contradict what is explicitly disclosed. These macromers are characterized by having at least two polymerizable groups, separated by at least one degradable region. Preferred applications for the hyrdogels include prevention of adhesion formation after surgical procedures, controlled release of drugs and other bioactive species, temporary protection or separation of tissue surfaces, adhering of sealing tissues together, and preventing the attachment of cells to tissue surfaces. Example 13 is directed to nerve tissues and Example 14 is directed to muscle tissues.

Synthetic precursors may be used. Synthetic refers to a molecule not found in nature or not normally found in a human. Some synthetic precursors are free of amino acids or free of amino acid sequences that occur in nature. Some synthetic precursors are polypeptides that are not found in nature or are not normally found in a human body, e.g., di-, tri-, or tetra-lysine. Some synthetic molecules have amino acid residues but only have one, two, or three that are contiguous, with the amino acids or clusters thereof being separated by non-natural polymers or groups. Polysaccharides or their derivatives are thus not synthetic.

Alternatively, natural proteins or polysaccharides may be adapted for use with these methods, e.g., collagens, fibrin (ogen)s, albumins, alginates, hyaluronic acid, and heparins. These natural molecules may further include chemical derivitization, e.g., synthetic polymer decorations. The natural molecule may be crosslinked via its native nucleophiles or after it is derivatized with functional groups, e.g., as in U.S. Pat. Nos. 5,304,595, 5,324,775, 6,371,975, and 7,129,210, each of which is hereby incorporated by reference to the extent it does not contradict what is explicitly disclosed herein. Natural refers to a molecule found in nature. Natural polymers, for example proteins or glycosaminoglycans, e.g., collagen, fibrinogen, albumin, and fibrin, may be crosslinked using reactive precursor species with electrophilic functional groups. Natural polymers normally found in the body are proteolytically degraded by proteases present in the body. Such polymers may be reacted via functional groups such as amines, thiols, or carboxyls on their amino acids or derivatized to have activatable functional groups. While natural polymers may be used in hydrogels, their time to gelation and ultimate mechanical properties must be controlled by appropriate introduction of additional functional groups and selection of suitable reaction conditions, e.g., pH.

Precursors may be made with a hydrophobic portion provided that the resultant hydrogel retains the requisite amount of water, e.g., at least about 20%. In some cases, the precursor is nonetheless soluble in water because it also has a hydrophilic portion. In other cases, the precursor makes dispersion in the water (a suspension) but is nonetheless reactable to from a crosslinked material. Some hydrophobic portions may include a plurality of alkyls, polypropylenes, alkyl chains, or other groups. Some precursors with hydrophobic portions are sold under the trade names PLURONIC F68, JEFFAMINE, or TECTRONIC. A hydrophobic portion is one that is sufficiently hydrophobic to cause the macromer or copolymer to aggregate to form micelles in an aqueous continuous phase or one that, when tested by itself, is sufficiently hydrophobic to precipitate from, or otherwise change phase while within, an aqueous solution of water at pH from about 7 to about 7.5 at temperatures from about 30 to about 50 degrees Centigrade.

Precursors may have, e.g., 2-100 arms, with each arm having a terminus, bearing in mind that some precursors may be dendrimers or other highly branched materials. An arm on a hydrogel precursor refers to a linear chain of chemical groups that connect a crosslinkable functional group to a polymer core. Some embodiments are precursors with between 3 and 300 arms; artisans will immediately appreciate that all the ranges and values within the explicitly stated ranges are contemplated, e.g., 4 to 16, 8 to 100, or at least 6 arms.

Thus hydrogels can be made, e.g., from a multi-armed precursor with a first set of functional groups and a low molecular-weight precursor having a second set of functional groups. For example, a six-armed or eight-armed precursor may have hydrophilic arms, e.g., polyethylene glycol, terminated with primary amines, with the molecular weight of the arms being about 1,000 to about 40,000; artisans will immediately appreciate that all ranges and values within the explicitly stated bounds are contemplated. Such precursors may be mixed with relatively smaller precursors, for example, molecules with a molecular weight of between about 100 and about 5000, or no more than about 800, 1000, 2000, or 5000 having at least about three functional groups, or between about 3 to about 16 functional groups; ordinary artisans will appreciate that all ranges and values between these explicitly articulated values are contemplated. Such small molecules may be polymers or nonpolymers and natural or synthetic.

Precursors that are not dendrimers may be used. Dendritic molecules are highly branched radially symmetrical polymers in which the atoms are arranged in many arms and subarms radiating out from a central core. Dendrimers are characterized by their degree of structural perfection as based on the evaluation of both symmetry and polydispersity and require particular chemical processes to synthesize. Accordingly, an artisan can readily distinguish dendrimer precursors from non-dendrimer precursors. Dendrimers have a shape that is typically dependent on the solubility of its component polymers in a given environment, and can change substantially according to the solvent or solutes around it, e.g., changes in temperature, pH, or ion content.

Precursors may be dendrimers, e.g., as in Patent Application Pub. Nos. US 20040086479, US 20040131582, WO 07005249, WO 07001926, WO 06031358, or the U.S. counterparts thereof; dendrimers may also be useful as multifunctional precursors, e.g., as in U.S. Pat. Pub. No's. US 20040131582, US 20040086479 and PCT Applications No. WO 06031388 and WO 06031388; each of which US and PCT applications are hereby incorporated by reference herein in its entirety to the extent they do not contradict what is explicitly disclosed herein. Dendrimers are highly ordered possess high surface area to volume ratios, and exhibit numerous end groups for potential functionalization. Embodiments include multifunctional precursors that are not dendrimers.

Some embodiments include a precursor that consists essentially of an oligopeptide sequence of no more than five residues, e.g., amino acids comprising at least one amine, thiol, carboxyl, or hydroxyl side chain. A residue is an amino acid, either as occurring in nature or derivatized thereof. The backbone of such an oligopeptide may be natural or synthetic. In some embodiments, peptides of two or more amino acids are combined with a synthetic backbone to make a precursor; certain embodiments of such precursors have a molecular weight in the range of about 100 to about 10,000 or about 300 to about 500 Artisans will immediately appreciate that all ranges and values between these explicitly articulated bounds are contemplated.

Precursors may be prepared to be free of amino acid sequences cleavable by enzymes present at the site of introduction, including free of sequences susceptible to attach by metalloproteinases and/or collagenases. Further, precursors may be made to be free of all amino acids, or free of amino acid sequences of more than about 50, 30, 20, 10, 9, 8, 7, 6, 5, 4, 3, 2, or 1 amino acids. Precursors may be non-proteins, meaning that they are not a naturally occurring protein and cannot be made by cleaving a naturally occurring protein and cannot be made by adding synthetic materials to a protein. Precursors may be non-collagen, non-fibrin, non-fibrinogen), and non-albumin, meaning that they are not one of these proteins and are not chemical derivatives of one of these proteins. The use of non-protein precursors and limited use of amino acid sequences can be helpful for avoiding immune reactions, avoiding unwanted cell recognition, and avoiding the hazards associated with using proteins derived from natural sources. Precursors can also be non-saccharides (free of saccharides) or essentially non-saccharides (free of more than about 5% saccharides by w/w of the precursor molecular weight. Thus a precursor may, for example, exclude hyaluronic acid, heparin, or gellan. Precursors can also be both non-proteins and non-saccharides.

Peptides may be used as precursors. In general, peptides with less than about 10 residues are preferred, although larger sequences (e.g., proteins) may be used. Artisans will immediately appreciate that every range and value within these explicit bounds is included, e.g., 1-10, 2-9, 3-10, 1, 2, 3, 4, 5, 6, or 7. Some amino acids have nucleophilic groups (e.g., primary amines or thiols) or groups that can be derivatized as needed to incorporate nucleophilic groups or electrophilic groups (e.g., carboxyls or hydroxyls). Polyamino acid polymers generated synthetically are normally considered to be synthetic if they are not found in nature and are engineered not to be identical to naturally occurring biomolecules.

Some hydrogels are made with a polyethylene glycol-containing precursor. Polyethylene glycol (PEG, also referred to as polyethylene oxide when occurring in a high molecular weight) refers to a polymer with a repeat group $(CH_2CH_2O)_n$, with n being at least 3. A polymeric precursor having a polyethylene glycol thus has at least three of these repeat groups connected to each other in a linear series. The polyethylene glycol content of a polymer or arm is calculated by adding up all of the polyethylene glycol groups on the polymer or arm, even if they are interrupted by other groups. Thus, an arm having at least 1000 MW polyethylene glycol has enough $CH_2CH_2O$ groups to total at least 1000 MW. As is customary terminology in these arts, a polyethylene glycol polymer does not necessarily refer to a molecule that terminates in a hydroxyl group. Molecular weights are abbreviated in thousands using the symbol k, e.g., with 15K meaning 15,000 molecular weight, i.e., 15,000 Daltons. SG or SGA refers to succinimidyl glutarate. SS refers to succinate succinimide. SS and SG are succinimidyl esters that have an ester group that degrades by hydrolysis in water. Hydrolytically degradable thus refers to a material that would spontaneously degrade in vitro in an excess of water without any enzymes or cells present to mediate the degradation. A time for degradation refers to effective disappearance of the material as judged by the naked eye. Trilysine (also abbreviated LLL) is a synthetic tripeptide. PEG and/or hydrogels may be provided in a form that is pharmaceutically acceptable, meaning that it is highly purified and free of contaminants, e.g., pyrogens.

Functional Groups

The precursors have functional groups that react with each other to form the material, either outside a patient, or in situ. The functional groups generally have polymerizable groups for polymerization or react with each other in electrophile-nucleophile reactions or are configured to participate in other polymerization reactions. Various aspects of polymerization reactions are discussed in the precursors section herein.

Thus in some embodiments, precursors have a polymerizable group that is activated by photoinitiation or redox systems as used in the polymerization arts, e.g., or electrophilic functional groups that are carbodiimidazole, sulfonyl chloride, chlorocarbonates, n-hydroxysuccinimidyl ester, succinimidyl ester or sulfasuccinimidyl esters, or as in U.S. Pat. Nos. 5,410,016, or 6,149,931, each of which are hereby incorporated by reference herein in its entirety to the extent they do not contradict what is explicitly disclosed herein. The nucleophilic functional groups may be, for example, amine, hydroxyl, carboxyl, and thiol. Another class of electrophiles are acyls, e.g., as in U.S. Pat. No. 6,958,212, which describes, among other things, Michael addition schemes for reacting polymers.

Certain functional groups, such as alcohols or carboxylic acids, do not normally react with other functional groups, such as amines, under physiological conditions (e.g., pH 7.2-11.0, 37° C.). However, such functional groups can be made more reactive by using an activating group such as N-hydroxysuccinimide. Certain activating groups include carbonyldiimidazole, sulfonyl chloride, aryl halides, sulfosuccinimidyl esters, N-hydroxysuccinimidyl ester, succinimidyl ester, epoxide, aldehyde, maleimides, imidoesters and the like. The N-hydroxysuccinimide esters or N-hydroxysulfosuccinimide (NHS) groups are useful groups for crosslinking of proteins or amine-containing polymers, e.g., amino terminated polyethylene glycol. An advantage of an NHS-amine reaction is that the reaction kinetics are favorable, but the gelation rate may be adjusted through pH or concentration. The NHS-amine crosslinking reaction leads to formation of N-hydroxysuccinimide as a side product. Sulfonated or ethoxylated forms of N-hydroxysuccinimide have a relatively increased solubility in water and hence their rapid clearance from the body. An NHS-amine crosslinking reaction may be carried out in aqueous solutions and in the presence of buffers, e.g., phosphate buffer (pH 5.0-7.5), triethanolamine buffer (pH 7.5-9.0), or borate buffer (pH 9.0-12), or sodium bicarbonate buffer (pH 9.0-10.0). Aqueous solutions of NHS based crosslinkers and functional polymers preferably are made just before the crosslinking reaction due to reaction of NHS groups with water. The reaction rate of these groups may be delayed by keeping these solutions at lower pH (pH 4-7). Buffers may also be included in the hydrogels introduced into a body.

In some embodiments, each precursor comprises only nucleophilic or only electrophilic functional groups, so long as both nucleophilic and electrophilic precursors are used in the crosslinking reaction. Thus, for example, if a crosslinker has nucleophilic functional groups such as amines, the functional polymer may have electrophilic functional groups such as N-hydroxysuccinimides. On the other hand, if a crosslinker has electrophilic functional groups such as sulfosuccinimides, then the functional polymer may have nucleophilic functional groups such as amines or thiols. Thus, functional polymers such as proteins, poly(allyl amine), or amine-terminated di-or multifunctional poly(ethylene glycol) can be used.

One embodiment has reactive precursor species with 3 to 16 nucleophilic functional groups each and reactive precursor species with 2 to 12 electrophilic functional groups each; artisans will immediately appreciate that all the ranges and values within the explicitly stated ranges are contemplated.

The functional groups may be, e.g., electrophiles reactable with nucleophiles, groups reactable with specific nucleophiles, e.g., primary amines, groups that form amide bonds with materials in the biological fluids, groups that form amide bonds with carboxyls, activated-acid functional groups, or a combination of the same. The functional groups may be, e.g., a strong electrophilic functional group, meaning an electrophilic functional group that effectively forms a covalent bond with a primary amine in aqueous solution at pH 9.0 at room temperature and pressure and/or an electrophilic group that reacts by a of Michael-type reaction. The strong electrophile may be of a type that does not participate in a Michaels-type reaction or of a type that participates in a Michaels-type reaction.

A Michael-type reaction refers to the 1, 4 addition reaction of a nucleophile on a conjugate unsaturated system. The addition mechanism could be purely polar, or proceed through a radical-like intermediate state(s); Lewis acids or appropriately designed hydrogen bonding species can act as catalysts. The term conjugation can refer both to alternation of carbon-carbon, carbon-heteroatom or heteroatom-heteroatom multiple bonds with single bonds, or to the linking of a functional group to a macromolecule, such as a synthetic polymer or a protein. Michael-type reactions are discussed in detail in U.S. Pat. No. 6,958,212, which is hereby incorporated by reference herein in its entirety for all purposes to the extent it does not contradict what is explicitly disclosed herein.

Examples of strong electrophiles that do not participate in a Michaels-type reaction are: succinimides, succinimidyl esters, or NHS-esters. Examples of Michael-type electrophiles are acrylates, methacrylates, methylmethacrylates, and other unsaturated polymerizable groups.

Initiating Systems

Some precursors react using initiators. An initiator group is a chemical group capable of initiating a free radical polymerization reaction. For instance, it may be present as a separate component, or as a pendent group on a precursor. Initiator groups include thermal initiators, photoactivatable initiators, and oxidation-reduction (redox) systems. Long wave UV and visible light photoactivatable initiators include, for example, ethyl eosin groups, 2, 2-dimethoxy-2-phenyl acetophenone groups, other acetophenone derivatives, thioxanthone groups, benzophenone groups, and camphorquinone groups. Examples of thermally reactive initiators include 4, 4' azobis (4-cyanopentanoic acid) groups, and analogs of benzoyl peroxide groups. Several commercially available low temperature free radical initiators, such as V-044, available from Wako Chemicals USA, Inc., Richmond, Va., may be used to initiate free radical crosslinking reactions at body temperatures to form hydrogel coatings with the aforementioned monomers.

Metal ions may be used either as an oxidizer or a reductant in redox initiating systems. For example, ferrous ions may be used in combination with a peroxide or hydroperoxide to initiate polymerization, or as parts of a polymerization system. In this case, the ferrous ions would serve as a reductant. Alternatively, metal ions may serve as an oxidant. For example, the ceric ion (4+ valence state of cerium) interacts with various organic groups, including carboxylic acids and urethanes, to remove an electron to the metal ion, and leave an initiating radical behind on the organic group. In such a system, the metal ion acts as an oxidizer. Potentially suitable metal ions for either role are any of the transition metal ions, lanthanides and actinides, which have at least two readily accessible oxidation states. Particularly useful metal ions have at least two states separated by only one difference in charge. Of these, the most commonly used are ferric/ferrous; cupric/cuprous; ceric/cerous; cobaltic/cobaltous; vanadate V vs. IV; permanganate; and manganic/manganous. Peroxygen containing compounds, such as peroxides and hydroperoxides, including hydrogen peroxide, t-butyl hydroperoxide, t-butyl peroxide, benzoyl peroxide, cumyl peroxide may be used.

An example of an initiating system is the combination of a peroxygen compound in one solution, and a reactive ion, such as a transition metal, in another. In this case, no external initiators of polymerization are needed and polymerization proceeds spontaneously and without application of external energy or use of an external energy source when two complementary reactive functional groups containing moieties interact at the application site.

Hydrogels and Hydrogel Formation

In general, the precursors may be combined to make a covalently-crosslinked hydrogel. The hydrogel may comprise a therapeutic agent, or agents, released over a suitable period of time. Hydrogels may be made beforehand or in situ.

When made in situ, the crosslinking reactions generally occur in aqueous solution under physiological conditions. The crosslinking reactions preferably do not release heat of polymerization or require exogenous energy sources for initiation or to trigger polymerization. Formation of hydrogels in situ can result in adherence of the hydrogel to the tissue margins. This adherence will tend to reduce fluid flow into the cavity by the bridging of native molecules across the hydrogel barrier and thereby advantageously reduce seroma formation.

The data of Examples 1 and 2 indicates that the hydrogel swelled in place. An embodiment is a hydrogel with less swelling. The hydrogel may be generally low-swelling, as measurable by the hydrogel having a weight increasing no more than about 50% upon exposure to a physiological solution in the absence of physical restraints for twenty-four hours relative to a weight of the hydrogel at the time of formation. Swelling may be measured or expressed by weight or volume. Some embodiments swell by weight or by volume no more than about 50%, no more than about 20%, or no more than about 0%; artisans will immediately appreciate that all the ranges and values within the explicitly stated ranges are contemplated, e.g., shrinkage from 10% to 20% (negative swelling), swelling from −10% to no more than 50%. One aspect of swelling is that large changes will increase the difficulty of achieving a desired hydrogel size. For instance, filling a depression in a tissue with a swelling hydrogel will cause the hydrogel to have a height that is not apparent to the user at the time of application and/or gelation. Similarly, swelling (and shrinkage) can create forces that tend to pull the hydrogel away from surrounding tissues so that adherence is affected.

One approach for low-swelling is increase the number of crosslinks or solids content. Increasing in these factors, however, will typically effect the mechanical properties of the gel, with more crosslinks making the gel more brittle but stronger and a higher solids content making the gel stronger. These factors can also increase degradation time and may affect interactions with cells. Another embodiment to reduce swelling is to choose precursors that have a high degree of solvation at the time of crosslinking but subsequently become less solvated and having a radius of solvation that effectively shrinks; in other words, the precursor is spread-out in solution when crosslinked but later contracts. Changes to pH, temperature, solids concentration, and solvent environment can cause such changes; moreover, an increase in the number of branches (with other factors being held effectively constant) will tend to also have this effect. The number of arms are believed to sterically hinder each other so that they spread-out before crosslinking, but these steric effects are offset by other factors after polymerization. In some embodiments, precursors have a plurality of similar charges so as to achieve these effects, e.g., a plurality of functional groups having a negative charge, or a plurality of arms each having a positive charge, or each arm having a functional group of similar charges before crosslinking or other reaction.

Hydrogels described herein can include hydrogels that swell minimally after deposition. Such medical low-swellable hydrogels may have a weight upon polymerization that increases no more than, e.g., about 25%, about 10%, about 5%, about 0% by weight upon exposure to a physiological solution, or that shrink (decrease in weight and volume), e.g., by at least about 5%, at least about 10%, or more. Artisans will immediately appreciate that all ranges and values within or otherwise relating to these explicitly articulated limits are disclosed herein. Unless otherwise indicated, swelling of a hydrogel relates to its change in volume (or weight) between the time of its formation when crosslinking is effectively complete and the time after being placed in in vitro aqueous solution in an unconstrained state for twenty-four hours, at which point it may be reasonably assumed to have achieved its equilibrium swelling state. For most embodiments, cros slinking is effectively complete within no more than about three minutes such that the initial weight can generally be noted at about 15 minutes after formation as Weight at initial formation. Accordingly, this formula is used: % swelling=[(Weight at 24 hours−Weight at initial formation)/Weight at initial formation]*100. The weight of the hydrogel includes the weight of the solution in the hydrogel.

Reaction kinetics are generally controlled in light of the particular functional groups, their concentrations, and the local pH unless an external initiator or chain transfer agent is required, in which case triggering the initiator or manipulating the transfer agent can be a controlling step. In some embodiments, the molecular weights of the precursors are used to affect reaction times. Precursors with lower molecular weights tend to speed the reaction due to their higher concentration of reactive groups, so that some embodiments have at least one precursor with a molecular weight of less than about 1000 or about 2000 Daltons; artisans will immediately appreciate that all the ranges and values within the explicitly stated ranges are contemplated, e.g., from 100 to about 900 Daltons or from 500 to about 1800 Daltons.

The crosslinking density of the resultant biocompatible crosslinked polymer is controlled by the overall molecular weight of the crosslinker and functional polymer and the number of functional groups available per molecule. A lower molecular weight between crosslinks such as 500 will give much higher crosslinking density as compared to a higher molecular weight such as 10,000. The crosslinking density also may be controlled by the overall percent solids of the crosslinker and functional polymer solutions. Increasing the percent solids increases the probability that an electrophilic functional group will combine with a nucleophilic functional group prior to inactivation by hydrolysis. Yet another method to control crosslink density is by adjusting the stoichiometry of nucleophilic functional groups to electrophilic functional groups. A one to one ratio leads to the highest crosslink density. Precursors with longer distances between crosslinks are generally softer, more compliant, and more elastic. Thus an increased length of a water-soluble segment, such as a polyethylene glycol, tends to enhance elasticity to produce desirable physical properties. Thus certain embodiments are directed to precursors with water soluble segments having molecular weights in the range of 3,000 to 100,000; artisans will immediately appreciate that all the ranges and values within the explicitly stated ranges are contemplated e.g., 10,000 to 35,000.

The solids content of the hydrogel can affect its mechanical properties and biocompatibility and reflects a balance between competing requirements. A relatively low solids content is useful, e.g., between about 2.5% to about 20%, including all ranges and values there between, e.g., about 2.5% to about 10%, about 5% to about 15%, or less than about 15%.

An embodiment for making a hydrogel in situ in the presence of a therapeutic agent is to combine precursors in an aqueous solution that can be administered with an applicator to the punctum and/or canaliculus and thereafter form the hydrogel. The precursors may be mixed with an activating agent before, during, or after administration. The hydrogel may be placed with a therapeutic agent dispersed therein, e.g., as a solution, suspension, particles, micelles, or encapsulated. Crosslinking, in one embodiment, entraps the agent. In another embodiment, the crosslinking causes the agent to precipitate or move from solution to suspension.

Thus one embodiment relates to combining a first hydrogel precursor with a first type of functional groups with a second hydrogel precursor having a second type of functional groups in an aqueous solvent in the presence of a therapeutic agent in the solvent. In one embodiment, the precursors are dissolved separately and combined in the presence of an activating agent that provides for effective crosslinking. Alternatively, the mere mixing of the precursors triggers crosslinking. Accordingly, one embodiment is providing branched polymer having a plurality of succinimidyl termini dissolved in a low pH (4.0) diluent solution) containing a low molecular weight precursor comprising nucleophiles. This solution is activated by combination with a higher pH solution (8.8), initiating the crosslinking mechanism. The agent is pre-loaded as a suspension in the diluent solution. The gel forms in situ.

Overview of Other Systems

Certain polymerizable hydrogels made using synthetic precursors are known in the medical arts, e.g., as used in products such as FOCALSEAL (Genzyme, Inc.), COSEAL (Angiotech Pharmaceuticals), and DURASEAL (Confluent Surgical, Inc.), as in, for example, U.S. Pat. Nos. 6,656,200; 5,874,500; 5,543,441; 5,514,379; 5,410,016; 5,162,430; 5,324,775; 5,752,974; and 5,550,187; each of which are hereby incorporated by reference to the extent they do not contradict what is explicitly disclosed herein. These materials can polymerize too quickly to be injected in a controlled fashion for at least some of the applications described herein. Also, COSEAL and DURASEAL have a high pH, (above pH 9). Another reason is that they apparently swell too much for filling of iatrogenic sites. The swelling of COSEAL and DURASEAL has been measured using an in vitro model in comparison to fibrin sealant (Campbell et al., Evaluation of Absorbable Surgical Sealants: In vitro Testing, 2005). Over a three day test, COSEAL swelled an average of about 558% by weight, DURASEAL increased an average of about 98% by weight, and fibrin sealant swelled about 3%. Assuming uniform expansion along all axes, the percent increase in a single axis was calculated to be 87%, 26%, and 1% for COSEAL, DURASEAL, and fibrin sealant respectively. FOCALSEAL is known to swell over 300%. And it also needs an external light to be activated. Fibrin sealant is a proteinaceous glue that has adhesive, sealing, and mechanical properties that are inferior to COSEAL, DURASEAL, and other hydrogels disclosed herein. Further, it is typically derived from biological sources that are potentially contaminated, is cleared from the body by mechanisms distinct from water-degradation, and typically requires refrigeration while stored.

Radioopaque Agents for Hydrogels

Some hydrogel applications would be facilitated if the hydrogel included radioopaque (RO) agents. These agents may be mixed with the hydrogel and/or covalently attached.

One embodiment involves using branched precursors that have a covalently attached RO agent, so that the hydrogel will have the RO agent covalently attached upon its formation from mixtures of, or including, the RO-labeled precursor.

Examples 3 and 4 demonstrate techniques for incorporation of such agents into a matrix. One issue is the need for the RO agent to be present in adequate concentration and volume. The amount of agent that is helpful can depend on the tissue site and imaging method. A CT number (also referred to as a Hounsfield unit or number) is a measure of visibility under indirect imaging techniques. A CT number was determined for various concentrations of the RO agent iohexol, which contains iodine, FIG. 8.

A CT number of at least about 90 may be used. Embodiments include providing a matrix (e.g., hydrogel) with a concentration of RO agent to give a CT number of more than about 50; artisans will immediately appreciate that all the ranges and values within the explicitly stated range is contemplated, e.g., at least about 80; about 90 to about 210, or from about 80 to about 2000. Embodiments also include an iodine concentration between about 0.05% and about 15%; artisans will immediately appreciate that all the ranges and values within the explicitly stated ranges are contemplated, e.g., from about 0.1% to about 3%.

For example, an 8-armed PEG precursor of about 10 k Daltons, with 5 of the 8 arms terminating in SG and 3 of the 8 arms bound to triiodobenzoate (TIB) at a concentration of 2% gel solids will have about 0.18% iodine in the gel and 93 HU, compared to a 20% gel solids gel with 1.8% iodine in the gel and about 700 HU. 4-arm (Example 3) and 8-arm (Example 4) branched precursor molecules had some of their arms bound with TIB, a molecule that contains three iodines. The other PEG arms without TIB were SG functionalized, allowing them to be cross linked with another precursor (trilysine in the Examples). Thus, the resulting hydrogels had radiopacity from the iodine, FIG. 9. The SG linkages are hydrolytically labile and thus degrade in water. Persistence of the iodine over a suitable time was addressed by controlling the number of functional groups that were derivitized with the RO agent.

Figure 9:
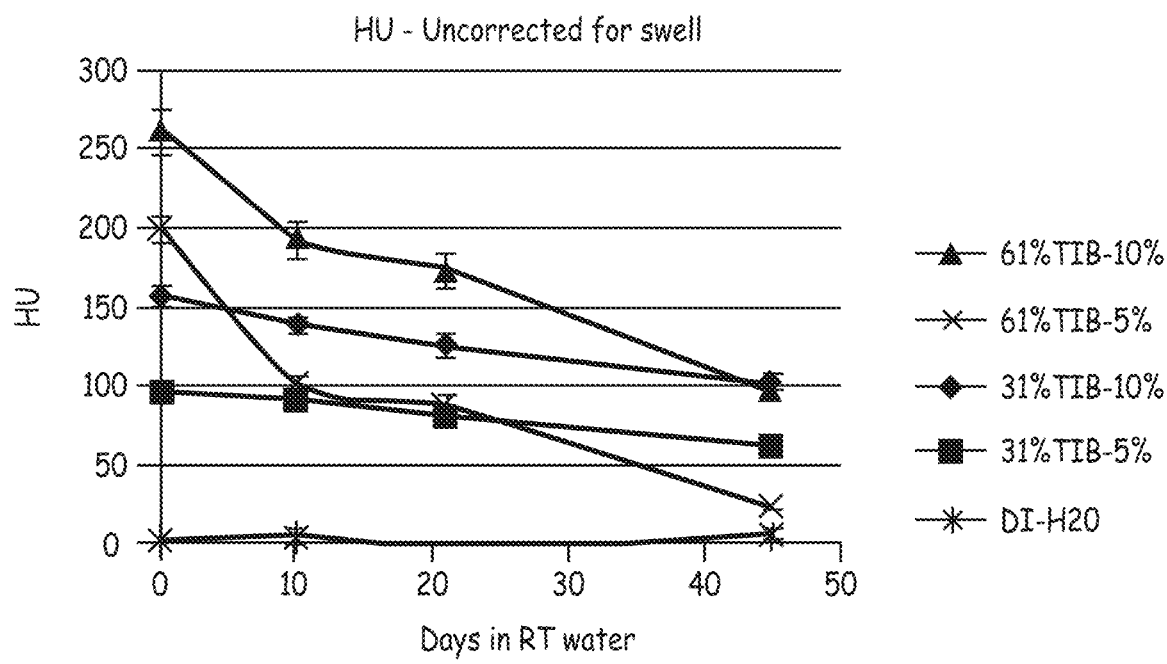
FIG. 9 is a plot depicting radiopacity of samples including hydrogels with bound iodine over time (Example 4), without correction for hydrogel swelling. The first percentage indicates the iodine (as TIB) substitution as a percentage of multi-armed precursor arms and the second percentage indicates the solids content of the hydrogel as a percent.
Figure 10:
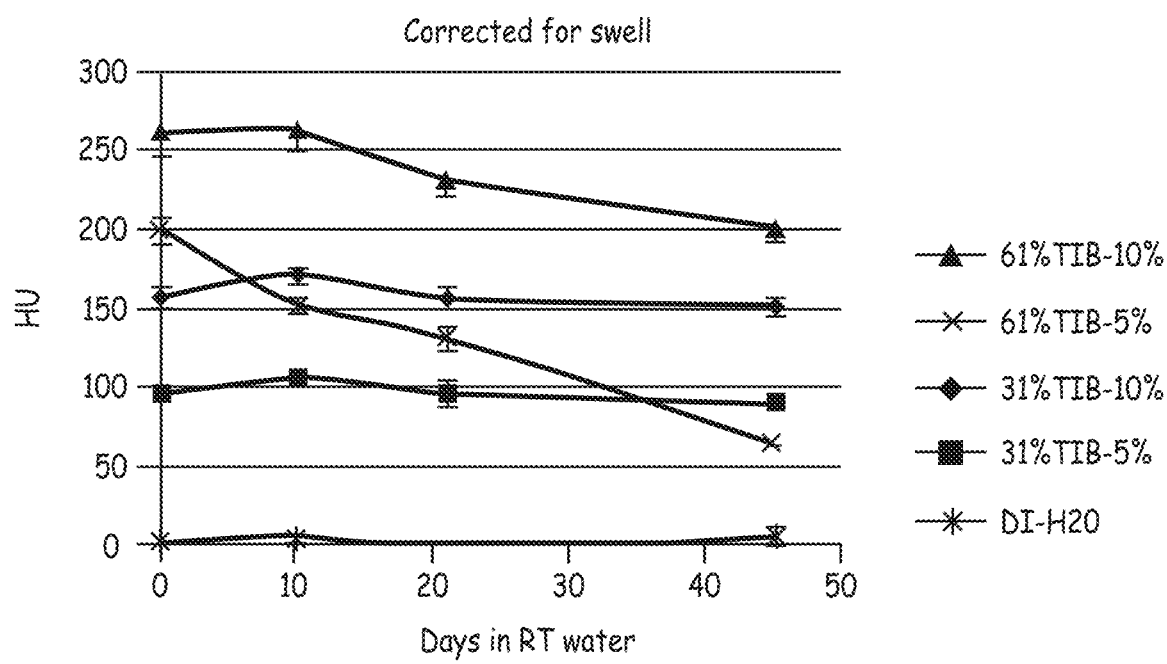
FIG. 10 is a plot depicting radiopacity of the samples of FIG. 9, with a correction for hydrogel swelling.

The presence of more than one link to the matrix provides for the RO agent to remain in the matrix and persist until hydrolysis results in the release and clearance of the precursor-TIB molecules, FIG. 9. Data from FIG. 10 shows RO matrices corrected for swell, and indicates iodine retention within the hydrogels. The decrease in RO seen in the 61% TIB samples is likely due to loss of PEG-TIB molecules, as those gels, with fewer SG linkages, are moving toward complete hydrolysis faster than the 31% TIB samples (the 61% TIB-5% has a faster rate than the 61% TIB-10%). The 31% TIB samples, with more SG linkages, appear to have a constant radiopacity, suggesting the loss of PEG-TIB has not started. Taken together this data suggests that the PEG-TIB linkage certainly withstands hydrolysis, and a hydrogel made with this linkage would be expected to retain RO agent, with potential losses due to swelling.

RO agents may be attached to precursors by a variety of methods. Some of these methods are set forth in U.S. Pat. No. 7,790,141, which is hereby incorporated by reference herein for all purposes, and including RO agents, precursors, and matrices; in case of conflict, this specification controls. Precursors set forth herein and in this incorporated reference may be decorated with one or more RO agents. In the case of a branched or multi-functional precursor, one or more of the available reactive sites may be left unreacted. Thus an 8-armed precursor may have between 1 and 8 functional groups available for covalent binding to form a matrix and between 1 and 8 functional groups replaced by (or reacted with) RO agents. Examples of RO agents are molecules comprising iodine, TIB, phenyl ring compounds such as 2, 3, 5-triiodobenzoic acid, 3, 4, 5-triiodophenol, erythrosine, rose bengal, 3, 5-Bis(acetylamino)-2, 4, 6-triiodobenzoic acid, and 3, 5-Diacetamido-2, 4, 6-triiodobenzoic acid.

Additional machine-aided imaging agents may be used in addition to, or as alternatives to, radioopaque compounds. Such agents are, for example fluorescent compounds, ultrasonic contrast agents, or MRI contrast agents (e.g., Gadolinium containing compounds).

Biodegradation

The hydrogel may be made water-degradable, as measurable by the hydrogel being dissolvable in vitro in an excess of water by degradation of water-degradable groups. This test is predictive of hydrolytically-driven dissolution in vivo, a process that is in contrast to cell or protease-driven degradation. Significantly, however, polyanhydrides or other conventionally-used degradable materials that degrade to acidic components tend to cause inflammation in tissues. The hydrogels, however, may exclude such materials, and may be free of polyanhydrides, anhydride bonds, or precursors that degrade into acid or diacids.

Instead, for example, SG (succinimidyl glutarate), SS (succinimidyl succinate), SC (succinimidyl carbonate), SAP (succinimidyl adipate), carboxymethyl hydroxybutyric acid (CM-HBA) may be used and have esteric linkages that are hydrolytically labile. More hydrophobic linkages such as suberate linkages may also be used, with these linkages being less degradable than succinate, glutarate or adipate linkages. Polyethylene glycols and other precursors may be prepared with these groups. The crosslinked hydrogel degradation may proceed by the water-driven hydrolysis of the biodegradable segment when water-degradable materials are used. Polymers that include ester linkages may also be included to provide a desired degradation rate, with groups being added or subtracted near the esters to increase or decrease the rate of degradation. Thus it is possible to construct a hydrogel with a desired degradation profile, from a few days to many months, using a degradable segment. If polyglycolate is used as the biodegradable segment, for instance, a crosslinked polymer could be made to degrade in about 1 to about 30 days depending on the crosslinking density of the network. Similarly, a polycaprolactone based crosslinked network can be made to degrade in about 1 to about 8 months. The degradation time generally varies according to the type of degradable segment used, in the following order: polyglycolate<polylactate<polytrimethylene carbonate<polycaprolactone. Thus it is possible to construct a hydrogel with a desired degradation profile, from a few days to many months, using a degradable segment.

The hydrogel may be water-degradable (hydrolytically degradable), as measurable by the hydrogel being dissolvable in vitro in an excess of water by degradation of water-degradable groups. This test is predictive of hydrolytically-driven dissolution in vivo, a process that is in contrast to cell or protease-driven degradation. The hydrogels can be selected to be absorbable over days, weeks, or months.

A biodegradable linkage in the hydrogel and/or precursor may be water-degradable or enzymatically degradable. Illustrative water-degradable biodegradable linkages include polymers, copolymers and oligomers of glycolide, dl-lactide, l-lactide, dioxanone, esters, carbonates, and trimethylene carbonate. Illustrative enzymatically biodegradable linkages include peptidic linkages cleavable by metalloproteinases and collagenases. Examples of biodegradable linkages include polymers and copolymers of poly(hydroxy acid)s, poly(orthocarbonate)s, poly(anhydride)s, poly(lactone)s, poly(aminoacid)s, poly(carbonate)s, and poly(phosphonate)s.

If it is desired that a biocompatible crosslinked matrix be biodegradable or absorbable, one or more precursors having biodegradable linkages present in between the functional groups may be used. The biodegradable linkage optionally also may serve as the water soluble core of one or more of the precursors used to make the matrix. For each approach, biodegradable linkages may be chosen such that the resulting biodegradable biocompatible crosslinked polymer will degrade or be absorbed in a desired period of time.

Matrix materials may be chosen so that degradation products are absorbed into the circulatory system and essentially cleared from the body via renal filtration. The matrix materials may be hydrogels. One method is to choose precursors that are not broken down in the body, with linkages between the precursors being degraded to return the precursors or precursors with small changes caused by the covalent crosslinking process. This approach is in contrast to choosing biological matrix materials that are destroyed by enzymatic processes and/or materials cleared by macrophages, or that result in by-products that are effectively not water soluble. Materials that are cleared from the body by renal filtration can be labeled and detected in the urine using techniques known to artisans. While there might be at least a theoretical loss of some of these materials to other bodily systems, the normal fate of the material is a kidney clearance process. The term essentially cleared thus refers to materials that are normally cleared through the kidneys.

Visualization Agents

A visualization agent may be used with the hydrogel; it reflects or emits light at a wavelength detectable to a human eye so that a user applying the hydrogel could observe the gel.

Some biocompatible visualization agents are FD&C BLUE #1, FD&C BLUE #2, and methylene blue. These agents are preferably present in the final electrophilic-nucleophilic reactive precursor species mix at a concentration of more than 0.05 mg/ml and preferably in a concentration range of at least 0.1 to about 12 mg/ml, and more preferably in the range of 0.1 to 4.0 mg/ml, although greater concentrations may potentially be used, up to the limit of solubility of the visualization agent. These concentration ranges can give a color to the hydrogel without interfering with crosslinking times (as measured by the time for the reactive precursor species to gel).

Visualization agents may be selected from among any of the various non-toxic colored substances suitable for use in medical implantable medical devices, such as FD&C BLUE dyes 3 and 6, eosin, methylene blue, indocyanine green, or colored dyes normally found in synthetic surgical sutures. The visualization agent may be present with either reactive precursor species, e.g., a crosslinker or functional polymer solution. The preferred colored substance may or may not become chemically bound to the hydrogel. The visualization agent may be used in small quantities, e.g., 1% weight/volume, more preferably less that 0.01% weight/volume and most preferably less than 0.001% weight/volume concentration; artisans will immediately appreciate that all the ranges and values within the explicitly stated ranges are contemplated.

Drugs or Other Therapeutic Agents for Delivery

The hydrogel or other matrix may be prepared with and used to deliver classes of drugs including steroids, non-steroidal anti-inflammatory drugs (NSAIDS), anti-cancer drugs, antibiotics, or others. The hydrogel may be used to deliver drugs and therapeutic agents, e.g., an anti-inflammatory (e.g., Diclofenac), a pain reliever (e.g., Bupivacaine), a Calcium channel blocker (e.g., Nifedipine), an Antibiotic (e.g., Ciprofloxacin), a Cell cycle inhibitor (e.g., Simvastatin), a protein (e.g., Insulin). The rate of release from the hydrogel will depend on the properties of the drug and the hydrogel, with factors including drug sizes, relative hydrophobicities, hydrogel density, hydrogel solids content, and the presence of other drug delivery motifs, e.g., microparticles.

The hydrogel precursor may be used to deliver classes of drugs including steroids, NSAIDS, antibiotics, pain relievers, inhibitors or vascular endothelial growth factor (VEGF), chemotherapeutics, antiviral drugs, for instance. The drugs themselves may be small molecules, proteins, RNA fragments, proteins, glycosaminoglycans, carbohydrates, nucleic acid, inorganic and organic biologically active compounds where specific biologically active agents include but are not limited to: enzymes, antibiotics, antineoplastic agents, local anesthetics, hormones, angiogenic agents, anti-angiogenic agents, growth factors, antibodies, neurotransmitters, psychoactive drugs, anticancer drugs, chemotherapeutic drugs, drugs affecting reproductive organs, genes, and oligonucleotides, or other configurations. The drugs that have low water solubility may be incorporated, e.g., as particulates or as a suspension. Higher water solubility drugs may be loaded within microparticles or liposomes. Microparticles can be formed from, e.g., PLGA or fatty acids.

In some embodiments, the therapeutic agent is mixed with the precursors prior to making the aqueous solution or during the aseptic manufacturing of the functional polymer. This mixture then is mixed with the precursor to produce a crosslinked material in which the biologically active substance is entrapped. Functional polymers made from inert polymers like PLURONIC, TETRONICS or TWEEN surfactants may be used for releasing small molecule hydrophobic drugs.

In some embodiments, the therapeutic agent or agents are present in a separate phase when crosslinker and crosslinkable polymers are reacted to produce a matrix. This phase separation prevents participation of bioactive substance in the chemical crosslinking reaction such as reaction between NHS ester and amine group. The separate phase also can modulate the release kinetics of active agent from the crosslinked material or gel, where 'separate phase' could be oil (oil-in water emulsion), biodegradable vehicle, and the like. Biodegradable vehicles in which the active agent may be present include: encapsulation vehicles, such as microparticles, microspheres, microbeads, micropellets, and the like, where the active agent is encapsulated in a bioerodable or biodegradable polymers such as polymers and copolymers of: poly(anhydride), poly(hydroxy acid)s, poly(lactone)s, poly(trimethylene carbonate), poly(glycolic acid), poly(lactic acid), poly(glycolic acid)-co-poly(glycolic acid), poly(orthocarbonate), poly(caprolactone), crosslinked biodegradable hydrogel networks like fibrin glue or fibrin sealant, caging and entrapping molecules, like cyclodextrin, molecular sieves and the like. Microspheres made from polymers and copolymers of poly (lactone)s and poly (hydroxy acid) may be used as biodegradable encapsulation vehicles.

Visualization agents may be included, for instance, in the microspheres, microparticles, and/or microdroplets.

Embodiments of the invention include compositions and methods for forming matrices having entrapped therapeutic compounds. In one embodiment, a bioactive agent is entrapped in microparticles having a hydrophobic nature (also termed hydrophobic microdomains. In some cases, the resultant composite materials may have two phase dispersions, where both phases are absorbable, but are not miscible. For example, the continuous phase may be a hydrophilic network (such as a hydrogel, which may or may not be crosslinked) while the dispersed phase may be hydrophobic (such as an oil, fat, fatty acid, wax, fluorocarbon, or other synthetic or natural water immiscible phase, generically referred to herein as an "oil" or "hydrophobic" phase).

The oil phase entraps the drug and provides a barrier to release by partitioning of the drug into the hydrogel. The hydrogel phase in turn protects the oil from digestion by enzymes, such as lipases, and from dissolution by naturally occurring lipids and surfactants. The latter are expected to have only limited penetration into the hydrogel, for example, due to hydrophobicity, molecular weight, conformation, diffusion resistance, etc. In the case of a hydrophobic drug which has limited solubility in the hydrogel matrix, the particulate form of the drug may also serve as the release rate modifying agent. In one embodiment, a microemulsion of a hydrophobic phase and an aqueous solution of a water soluble molecular compound, such as a protein, peptide or other water soluble chemical is prepared. The emulsion is of the "water-in-oil" type (with oil as the continuous phase) as opposed to an "oil-in-water" system (where water is the continuous phase). Other aspects of drug delivery are found in U.S. Pat. Nos. 6,632,457; 6,379,373; and 6,514,534, each of which are hereby incorporated by reference, with the instant specification controlling in case of conflict. Moreover, drug delivery schemes as described in U.S. 2008/0187568 filed Feb. 6, 2008, which is hereby incorporated by reference herein (in case of conflict the present specification controls), may also be used with the hydrogels herein.

Controlled rates of drug delivery also may be obtained with the system disclosed herein by degradable, covalent attachment of the bioactive molecules to the crosslinked hydrogel network. The nature of the covalent attachment can be controlled to enable control of the release rate from hours to weeks or longer. By using a composite made from linkages with a range of hydrolysis times, a controlled release profile may be extended for longer durations.

Fiducial Marking

An application for the hydrogels is use as a fiduciary marker. Fiduciary markers are used in a wide range of medical imaging applications. Different images of the same object may be correlated by placing a fiduciary marker in the object. In radiotherapy, fiducial points are markers to facilitate correct targets for treatment. A radiation plan is developed to administer desired radiation doses to a tumor target site with due consideration given to limiting exposure of other tissues. Plans may be developed through simulations. Plans relate to the exact area that will be treated, the total radiation dose that will be delivered to the tumor, how much dose will be allowed for the normal tissues around the tumor, and the safest paths for radiation delivery. The plans are typically developed using computers with suitable software. Many checks should be made to ensure that the treatments are being delivered exactly as planned. The area selected for treatment usually includes the whole tumor plus healthy tissue around the tumor; these are the treatment margins. Radiation can come from a machine outside the body (external-beam radiation therapy) or from radioactive material placed in the body (brachytherapy).

Hydrogels as described herein may be used as fiduciary markers. Examples 1 and 2 describe hydrogels used fiduciary markers. The hydrogel was successfully used to completely fill lumpectomy cavities, partially fill cavities, and to mark cavities that were sutured closed. Examples 3 and 4 describe radioopaque (RO) agents used in combination with hydrogels. The RO agents enhance contrast with the surrounding tissue. Flowable precursors may be used to make the hydrogels in an iatrogenic site in situ. The precursors may be macromers, polymers, or monomers. The hydrogels may be made to be low-swelling. In general, precursors may be combined as described herein at an iatrogenic site to make a covalently-crosslinked material, e.g., a hydrogel that adheres to the margins of the site and has a stable shape. In cases where the lumpectomy cavity walls are opposed with sutures, as in oncoplasty procedures, the material can fill all the voids remaining in the cavity, still defining the cavity margins.

Embodiments thus include making a radiation plan using a hydrogel as a fiduciary marker. The plan may be in written form or stored in a computer readable medium. The term plan in this context refers to a product that can be exchanged in written or electronic form between persons and excludes intentions or other mental processes. Such plans may comprise a radiation dose or regimen and margin values. Similarly, a role as a fiducial marker may include imaging a site with a hydrogel repeatedly over time and in combination with providing radiation to the site. The site and marker may be imaged by a plurality of imaging devices as are typically used in the medical arts.

The hydrogels may be provided in flowable form to the site, e.g., as flowable precursors. The precursors may be dissolved in, or suspended in, a liquid and applied to the site. The precursors combine to form a hydrogel having a unitary continuous phase. Alternatively, the hydrogels may be provided as a plurality of particles that substantially contact each other, with the hydrogel phase being discontinuous. The particles may be made to have a lubricity and maximum diameter for manual passage out of a syringe through a 3 to 5 French catheter, or a 10 to 30 gauge needle. Artisans will immediately appreciate that all the ranges and values within the explicitly stated ranges are contemplated.

The hydrogels may be used to substantially fill a site. Substantially full means that the site is effectively full, with some allowances being made for elasticity of the site and packing of the hydrogel. The hydrogels may also be used to partially fill a site, e.g., from about 10% to about 90%; artisans will immediately appreciate that all the ranges and values within the explicitly stated ranges are contemplated.

A lumpectomy with a 3 cm diameter has a volume of about 14 cc, thus about 14 ml of hydrogel would be required to completely fill the cavity without excessive tension. Accordingly, the volume of the material may be tailored to the particular defect, e.g., from, about 1 ml to about 100 ml; artisans will immediately appreciate that all the ranges and values within the explicitly stated ranges are contemplated, e.g., from 6 ml to about 40 ml, or at least 5 ml. The implants tend to have a volume such that the implant includes at least one region with dimensions of more than $1 \times 1 \times 1$ cm or more than $1 \times 2 \times 2$ cm. Thus embodiments include implants formed in situ with at least one region having three dimensions each in the range of 1 to 3 cm; artisans will immediately appreciate that all the ranges and values within the explicitly stated ranges are contemplated, e.g., $1 \times 1 \times 2$ cm, $1 \times 2 \times 2$ cm, $3 \times 2 \times 1$ cm. The region may contain a continuous phase of matrix or packed particles. These embodiments are in contrast to other tissue matrices or coatings. By way of contrast, a layer of material that is only 5 mm thick would not contain a 1×1×1 cm region. Useful material features include tissue compatibility; the material is to be tissue compatible, with no systemic toxicity at high doses. Another feature is implant stability whereby dimensions do not appreciably change following implantation for a predetermined amount of time. Another feature is biodegradability: the hydrogel may gradually soften, liquefy and absorb after implantation.

Alternatively, the hydrogels may be fully or partially permanent and not biodegradable, e.g., for cosmetic applications such as breast or facial sites. Standard lumpectomies may result in a compromised cosmetic result, and often require whole breast irradiation due to imprecise tumor bed visualization.

Particles

One embodiment of the invention is directed to filling an iatrogenic site with a collection of particles that are small, pliable, and slippery so that they flow easily into a site and its irregularities, pack closely, provide stability, optionally are biodegradable, and provide good visualization of the margins.

One process for making particles involves creation of a matrix that is broken up to make the particles. Thus matrices, and matrices made with precursors as described herein, may be created and then broken up. One technique involves preparing the hydrogel and grinding it, e.g., in a ball mill or with a mortar and pestle. The matrix may be chopped or diced with knives or wires. Or the matrix could be cut-up in a blender. Another process involves forcing the hydrogels through a mesh, collecting the fragments, and passing them through the same mesh or another mesh until a desired size is reached.

The particles may be separated into collections with a desired size range and distribution of sizes by a variety of methods. Very fine control of sizing is available, with sizes ranging from 1 micron to several mm, and with a mean and range of particles sizes being controllable with a narrow distribution. Artisans will immediately appreciate that all the ranges and values within the explicitly stated ranges are contemplated. About 10 to about 500 microns is one such range that is useful, with sizes falling throughout the range of having a mean sizing at one value within the range, and a standard deviation centered around the mean value, e.g., from about 1% to about 100%. A simple method for sizing particles involves using custom-made or standardized mesh sizes. In addition to standard U.S. and Tyler mesh sizes, sieves are also commonly used in the Market Grade, Mill Grade, and Tensile Bolting Cloth. Hydrogels forced through meshes have been observed to show deformation so that the particle size is not precisely matched to mesh sizes; nonetheless, mesh sizes may be chosen to achieve a desired a particle size range. A spheroidal particle refers to a particle wherein the longest central axis (a straight line passing through the particle's geometric center) is no more than about twice the length of other central axes, with the particle being a literally spherical or having an irregular shape. A rod-shaped particle refers to a particle with a longitudinal central axis more than about twice the length of the shortest central axis.

Particles may also be made directly. In the case of ionic materials, well-controlled processes for making particles are known to artisans, for instance dropping small amounts of a polysaccharide into a bath of ions. Photopolymerization techniques are known for free radical polymerization, e.g., as in U.S. Pat. No. 5,410,016, which is hereby incorporated by reference herein; in case of conflict, the present specification controls. Emulsion-based techniques are also available. In one method, hydrogel microspheres are formed from polymerizable macromers or monomers by dispersion of a polymerizable phase in a second immiscible phase, wherein the polymerizable phase contains at least one component required to initiate polymerization that leads to cros slinking and the immiscible bulk phase contains another component required to initiate crosslinking, along with a phase transfer agent. Additionally, a polymerizable phase, containing all components for reaction, but with a slow polymerization rate, can be introduced into a second immiscible phase where it is dispersed into microspheres prior to polymerization. The polymerization arts also provide for micellar and microemulsion techniques for making particles.

A collection of microparticles may include sets of particles. For instance, some particles may be made to contain a radioopaque agent, with those particles forming a set within the collection. Other sets are directed to particle sizes, with the sets having distinct shapes or size distributions. As discussed, particles can be made with well-controlled sizes and divided into various sets for combination into a collection.

Particles with radioopaque agents may be blended with particles that are free of a radioopaque agent to make a collection of particles with a desired radiopacity. Example 3 details methods for making radioopaque hydrogels. The collection may thus have a percentage of iodine, for instance an amount that is between about 0.05% and 5%; artisans will immediately appreciate that all the ranges and values within the explicitly stated ranges are contemplated, e.g., from about 0.1% to about 0.4%. The iodine or other agent may be distributed between iodine covalently bound to the particles and/or iodine mixed into the particles (e.g., iodine mixed into the particles at the time of formation), and/or mixed with the particles (e.g., added to a solution that contains the particles). One or more radioopaque agents may be used to provide a collection with a target Hounsfield unit, e.g., more than about 50 or a value between about 50 and about 2000; artisans will immediately appreciate that all the ranges and values within the explicitly stated ranges are contemplated, e.g., more than about 90, from 80 to 800.

Other sets are directed to degradability. One embodiment involves a plurality of sets each having a distinct degradability profile. One application is the use of a plurality of sets with distinct degradability to promote tissue integration of an iatrogenic site. This technique may be used to reduce changes in shape of the surrounding tissue by allowing gradual tissue ingrowth as the particles degrade. One problem with iatrogenic sites is that they can contract or otherwise deform the surrounding tissue. For instance, in breast cancer, the removed tissue can cause a divot or otherwise poor cosmesis of the breast. A collection of particles that exhibits staged degradation, however, provides for tissue to grow into the space over time and provide a growth-filler. Some or all of the collection may be permanent and not degradable. Degradation times include 3 to 1000 days; artisans will immediately appreciate that all the ranges and values within the explicitly stated ranges are contemplated. For instance, a first set may have a median degradation time of from about 5 to about 8 days, a second set a median time of from about 30 to about 90 days, and a third set a median time of from about 180 to about 360 days.

The collections may optionally be prepared to be free of gas that may cause unwanted ultrasound echoes. One method involves simply degassing the particles under vacuum, with and/or without a liquid solvent. Ultrasound tends to visualize particles more than about 20 microns, depending on the wavelength that is used. Size ranges for particles include less than about 20 and less than about 20 microns. Alternatively, larger sized particles that have a high water content can also avoid echogenicity. Accordingly, embodiments include particles that essentially do not contribute to ultrasound images. In this context, essentially means that the particles do not interfere with the visualization of other bodily features, even if it is possible to sometimes discern the presence of the particles by ultrasound.

Collections may be made with sizes and lubricity for manual injection through a small gauge needle. Hydrophilic hydrogels crushed into spheroidal particles about 40 to about 100 microns diameter are small enough to be manually injected through a 30 gauge needle.

Hydrophilic hydrogel particles were observed to pass with difficulty through small gauge needles/catheters. The particle size contributes to resistance, as well as the viscosity of the solution. The particles tended to plug the needle. The resistance force is proportional to the viscosity of the fluid, with a more viscous fluid requiring more force to push through a small opening.

It was unexpectedly found, however, that increasing the viscosity of the solvent for the particles could lower the resistance to passage through a catheter and/or needle. This decrease may be attributed to using a solvent with a high osmolarity. Without being bound to a particular theory, the addition of these agents to improve injectability was caused by particle shrinkage, increased free water between particles which decreased particle-to-particle contributions to viscosity, and increased viscosity of the free water, which helped to pull the particles into and out of the syringes, preventing straining and plugging. The use of a linear polymer may further contribute thixotropic properties that are useful to prevent settling and encourage movement of the particles together with the solvent, but exhibit shear thinning when being forced out of a small opening. This approach was also observed to solve another problem, namely, a difficulty in moving particles from a solution through a needle/catheter since the particles tended to settle and otherwise elude pick-up. Expulsion through small bore openings of solutions of particles in aqueous solvent were observed; the solvent tended to move preferentially out of the applicator, leaving an excess of particles behind that could not be cleared from the applicator, or that plugged it, or in some instances could be cleared but only by use of an unsuitably large force not suited to an average user operating a hand-held syringe. The addition of osmotic agents, however, contributed viscosity and/or thixotropic behavior that helped to empty particles from an applicator. Embodiments of the invention include the addition of an osmotic agent to a plurality of particles. Examples of such agents include salts and polymers. Embodiments include polymers, linear polymers, and hydrophilic polymers, or combinations of the same. Embodiments include polymers of between about 500 and about 100,000 molecular weight; artisans will immediately appreciate that all the ranges and values within the explicitly stated ranges are contemplated, e.g., about 5000 to about 50,000 molecular weight. Embodiments include, for example, a concentration of about 1% to about 50% w/w osmotic agent; artisans will immediately appreciate that all the ranges and values within the explicitly stated ranges are contemplated, e.g., 10% to 30%. The agent and hydrogel may be introduced into a patient and may be part of a kit for the same.

Brachytherapy

Several brachytherapy techniques are used in cancer treatment. In brachytherapy, radioactive isotopes are sealed in pellets (seeds). These seeds are placed in patients. As the isotopes decay naturally, they give off radiation that damages nearby cancer cells. If left in place, after a few weeks or months, the isotopes decay completely and no longer give off radiation. The seeds will not cause harm if they are left in the body (permanent brachytherapy), although undesired migration from the site of the implant has been observed Brachytherapy can be given as a low-dose-rate or a high-dose-rate treatment: In low-dose-rate treatment, cancer cells receive continuous low-dose radiation from the source over a period of several days.

A conventional approach is a high-dose-rate brachytherapy source in balloon catheter placed in a lumpectomy site. In other words, balloons are placed into the cavity, and radioactive seeds are placed inside the balloon for discrete periods via a percutaneous attachment. Since there are many possible volumes of tissue, the clinician would generally select from a menu of sizes and pick the one that seems to be about the right size for the site. The MAMMOSITE System (Hologic) can be inserted during surgery, and allows for irradiation in 5 days of treatment. Negatives of this system include a high reported infection rate (12-16%) presumably due to the percutaneous access, patient issues such as discomfort and balloon rupture, and the need for extra equipment such as a high-dose-rate brachytherapy source, a shielded room, and other specialized equipment.

An embodiment of the invention is brachytherapy, with a radioactive seed or other source disposed with or inside a matrix in a cavity. The source may be disposed in a bulk hydrogel that is continuous, in a hydrogel particle, or mixed with hydrogel particles, or any combination thereof. The conformal positioning of the hydrogels provides significant advantages for providing radiation where it is needed. Moreover, the particles or matrices may be used in combination with MAMMOSITE or other radiation sources. The source may be present at the time of placement, in a mixture with hydrogel precursors or particles, or placed after the matrix or hydrogel is placed.

Breast brachytherapy may only proceed if there is adequate space between the balloon surface and the patient's skin. If inadequate distance between those surfaces is observed, the skin is sometimes damaged, or breast brachytherapy is curtailed. A hydrogel as described herein may be injected between the balloon surcease and the surrounding tissue and/or skin, effectively increasing that distance, allowing brachytherapy to proceed.

Tissue Augmentation

Hydrogels as set forth herein may be used for tissue augmentation. The use of collagen as for dermal augmentation is well known. Hydrogels, for example particulates, may be used for dermal filler or for tissue augmentation. Embodiments include injecting or otherwise placing a plurality of particles in a tissue, or forming a hydrogel in situ. The material may be injected or otherwise placed at the intended site.

Spacers

Hydrogels as set forth herein may be used to separate tissues to reduce a dose of radioactivity received by one of the tissues. As set forth in U.S. Pat. No. 7,744,913, which is hereby incorporated by reference herein for all purposes with the present specification controlling in case of conflict, spacer materials may be placed in a patient. Certain embodiments are a method comprising introducing a spacer to a position between a first tissue location and a second tissue location to increase a distance between the first tissue location and the second tissue location. Further, there may be a step of administering a dose of radioactivity to at least the first tissue location or the second tissue location. A method, for example, is delivering a therapeutic dose of radiation to a patient comprising introducing a biocompatible, biodegradable particulate hydrogel, e.g., a collection of particles optionally with radioopaque contents, between a first tissue location and a second tissue location to increase a distance between the first tissue location and the second tissue location, and treating the second tissue location with the therapeutic dose of radiation so that the presence of the filler device causes the first tissue location to receive less of the dose of radioactivity compared to the amount of the dose of radioactivity the first tissue location would receive in the absence of the spacer. The spacer may be introduced an injectable material and is a gel in the patient that is removed by biodegradation of the spacer in the patient. An example is the case wherein the first tissue location is associated with the rectum and the second tissue location is associated with the prostate gland. The amount of reduction in radiation can vary. Embodiments include at least about 10% to about 90%; artisans will immediately appreciate that all the ranges and values within the explicitly stated ranges are contemplated, e.g., at least about 50%.

The radiation may alternatively be directed to a third tissue so that the first tissue or the second tissue received a lower amount of radiation as a result of its separation from the other tissue(s). The first tissue and the second tissue may be adjacent to each other in the body, or may be separate from each other by other tissues.

Spacer volumes for separating tissues are dependent on the configuration of the tissues to be treated and the tissues to be separated from each other. In many cases, a volume of about 20 cubic centimeters (cc's or mls) is suitable. In other embodiments, as little as about 1 cc might be needed. Other volumes are in the range of about 5-1000 cc; artisans will immediately appreciate that all the ranges and values within the explicitly stated ranges are contemplated, e.g., 10-30 cc. In some embodiments, spacers are administered in two doses at different times so as to allow the tissues to stretch and accommodate the spacer and thereby receive a larger volumes of spacer than would otherwise be readily possible. Tissues to be separated by a spacer include, for example, at least one of a rectum, prostate, and breast, or a portion thereof. For instance, a first portion of a breast may be separated from a second portion.

Administration of Hydrogels

One mode of administration is to apply a mixture of precursors and other materials (e.g., therapeutic agent, viscosifying agent, accelerator, initiator) through a needle, cannula, catheter, or hollow wire to a iatrogenic site. The mixture may be delivered, for instance, using a manually controlled syringe or mechanically controlled syringe, e.g., a syringe pump. Alternatively, a dual syringe or multiple-barreled syringe or multi-lumen system may be used to mix the precursors at or near the site. Alternatively, a plurality of hydrogel particles may be applied instead of the precursors. Precursors and particles may also be mixed.

Either while the cavity is still open, or following oncoplasty and before skin closure, or after skin closure, a small gauge needle or a percutaneous catheter in the site can first be used to aspirate air or fluid, and then used to inject materials for the hydrogel, e.g., hydrogel particles or an in situ curing material. Injection at or near (within a few days or a few weeks) the time of surgery is distinct from, and provides a different outcome than, using the materials in a location that has undergone healing processes for a significant time. In this context, a few days includes 1 to 13 days and a few weeks includes 2 to 10 weeks; artisans will immediately appreciate that all the ranges and values within the explicitly stated ranges are contemplated. The precursors may be chosen so that degradation products are absorbed into the circulatory system and cleared from the body via renal filtration. One delivery embodiment is an applicator that consists of two syringes attached to a Y-connector with an integral static mixer. At implantation, precursors are injected from the syringes through a small, flexible catheter. Alternatively, a syringe of other application may be connected to the catheter and used to provide particles of hydrogel. The particles may be fully hydrated, partially hydrated, or desiccated. The catheter may be left in the suture line at the time of surgery and extend to the iatrogenic site. The catheter is removed after the hydrogel is delivered.

Alternatively, a needle or catheter may be used to deliver the hydrogel after the site is closed, optionally with indirect imaging for guiding the distal tip of the applicator to the intended site.

Applicators may be used in combination with the matrices and/or precursors. Kits or systems for making hydrogels may be prepared. The kits are manufactured using medically acceptable conditions and contain components that have sterility, purity and preparation that is pharmaceutically acceptable. The kit may contain an applicator as appropriate, as well as instructions. A therapeutic agent may be included pre-mixed or available for mixing. Solvents/solutions may be provided in the kit or separately, or the components may be pre-mixed with the solvent. The kit may include syringes and/or needles for mixing and/or delivery. The kit or system may comprise components set forth herein.

One system uses a dual container applicator, e.g., double barreled syringe, for delivering at least one precursor. One syringe may have least one precursor and the other syringe may have an activator for activating the precursor, e.g., an initiator. Or each syringe may have a precursor, with the precursors making a matrix as a result of mixing.

Another option for a kit or system is a collection of particles wherein at least some of the particles are dehydrated or are desiccated. One embodiment provides particles that are 30% to 100% desiccated; artisans will immediately appreciate that all the ranges and values within the explicitly stated ranges are contemplated. A kit may include one or more therapeutic agents that may optionally be mixed with the particles. For example, the kit may have a first agent and a second agent that are mixed with a half-desiccated set of particles in a solution so that the particles imbibe the solution and agent. A first set of particles may be mixed with a first agent and a second set with a second agent, or the agents may be mixed with a set of particles. The sets of particles with the imbibed agents may be further mixed with other particles to make a collection for placement into a patient.

Other embodiments provide a single applicator, e.g., one syringe that comprises particles for delivery. One embodiment provides a container for particle delivery (e.g., syringe barrel, vial with septum) that does not require the addition of further contents, e.g., the particles are used neat, or are already in a solution or slurry that will be placed into the patient. This allows for the use of injectable preformed hydrogel slurries, eliminating the need for reconstitution, multiple syringes, and allowing for stop-and-start injections without fear of needle plugging. The particle solvent may be essentially water, meaning about 99% v/v of the solvent is water, with salts or buffers being present as desired. Other solvents may be used that are safe and biocompatible, e.g., dimethylsulfoxide.

One method of treating a patient is directed to forming an implant that closely fills a cavity. The method relates to filling an iatrogenic site with at least one flowable material that flows into the site while substantially replacing the volume and shape of the removed material as determined by visual observation as the filling is performed. The material may comprise a collection of particles or a hydrogel precursor.

In some cases, a site may be revisited with a second procedure. This may involve re-operating the iatrogenic site to remove the matrix, surgically removing additional tissue, and repeating the method to form a new hydrogel. In some of these cases, the original hydrogel comprises a visually-observable visualization agent and removal of the hydrogel comprises aspirating the site until no more of the visualization agent is observable to the naked eye in the aspirate, with the visualization agent optionally being a dye, or a dye chosen from the group consisting of green and blue dyes.

EXAMPLES

Example 1

Conformal Filling with Hydrogels

Under an approved protocol, three cadaver specimens were obtained for bilateral lumpectomies; in one, unilateral lumpectomy was performed due to prior breast surgery. On the CT-simulation table, each specimen was positioned for left sided lumpectomy (using wedges). Lumpectomies ranging from 31 to 70 cc were performed. Following lumpectomy, a 0.25" diameter silicone catheter was placed within the cavity, the subcutaneous tissue was apposed, and the skin was closed. In one case, the superior and inferior cavity walls were apposed prior to closure. Before hydrogel injection, each underwent CT simulation (Philips BRILLIANCE BIG BORE CT, 3 mm slices, 120 kVp, 300 mA, 60 cm FOV).

Following CT simulation, 18 to 70 cc of hydrogel was injected within the cavity, the silicone catheter was withdrawn, and the hydrogel was allowed to solidify. The hydrogel, when injected, has the viscosity of water but then, within 60 seconds, polymerized and formed a soft, solid gel. The hydrogel was DURASEAL, which is commercially available and is formed from a multi-armed PEG reacted with trilysine.

In three cases, the injected volume was equal to the lumpectomy volume (63, 70, and 35 cc). In the other two cases, only 18 cc of PEG-hydrogel was injected (following 31 and 33 cc lumpectomies). CT-simulation was repeated. T2-weighted MR imaging was performed in the axial and sagittal planes (Siemens ESPREE 1.5T MRI, turbo spin-echo, TR 5.0 sec, TE 106 10 msec, FOV 26 cm, 3.0 mm slices, 256×256 matrix, 100% phase oversampling, 130 Hz/pixel, echo-train length 17). Then cone-beam CT imaging was performed (Elekta Synergy, XVI software v.4.1b21, 1024×1024 flat-panel detector, M10 collimator, BOWTIE filter, 120 kVp, nominal 40 mA/frame, nominal 40 ms/frame, 360 o scan, 410×410×120 reconstruction, isotropic 1 mm voxels). Finally, ultrasound imaging (7.1 MHz, B-K Medical 2101 FALCON, #8658 4-9 MHz probe) was performed. After all imaging was completed, gross dissection was performed to confirm hydrogel locations (FIG. 3).

The hydrogel clearly defined the lumpectomy cavity on multiple imaging modalities. An example from one lumpectomy procedure is shown (FIG. 3). On CT imaging (panel a), the homogeneous, water-density hydrogel contrasted well with the lower density breast tissue. With T2-weighted MRI (panel b), the hydrogel was hyperintense and very prominent compared with the surrounding tissue. On T1-weighted imaging, the hydrogel had a low signal-intensity and was not as conspicuous as on T2-weighted imaging. The lumpectomy cavity was also visible on cone-beam CT imaging (panel c). A corresponding gross axial section (panel d; hydrogel dyed blue to improve visualization for this study) showed very similar features as all three cross-sectional imaging modalities (note the flap of fat within the lumpectomy cavity). While ultrasound did not show as much cavity detail, the echolucent hydrogel contrasted well with the surrounding breast tissue (panel e).

The hydrogel was successfully used to completely fill lumpectomy cavities, partially fill cavities, and to mark cavities that were sutured closed. In three of the lumpectomy procedures, the cavity was filled with a volume of hydrogel equivalent to the volume of extracted tissue. For example, in FIGS. 3a and 3b, a 63 cc lumpectomy was performed and an equal volume of hydrogel was injected. The hydrogel completely filled the cavity and restored a normal, convex breast contour. However, in two cases, a smaller volume of hydrogel was injected (simply marking the cavity, rather than filling and expanding it). In FIGS. 3c and 3d, a 31 cc lumpectomy was injected with only 18 cc of hydrogel. While the hydrogel clearly marked the lumpectomy site, the cavity and breast surface remained concave. In one case, a 33 cc lumpectomy was performed and then (as is the preference of some breast surgeons), the superior and inferior walls of the cavity were sutured together. 18 cc of hydrogel was injected into this cavity, which marked the edges of the cavity, outlining the apposed tissue (FIGS. 3e and 3f). In each situation, the hydrogel still clearly defined the cavity location on both CT and MR imaging. In all 5 cases, gross dissection confirmed that the full extent of the cavity was marked by hydrogel.

Example 2

Radiation Exposure Control with Conformal Hydrogels

The specimens of Example 1 had radiation plans developed for pre-hydrogel implant cases and post-hydrogel implant cases. The pre-hydrogel and post-hydrogel CT scans were imported into a Pinnacle treatment planning system (v8.0m, Philips Radiation Oncology Systems). For first sets of plans, standard margin expansions (a 15 mm GTV-CTV expansion and a 10 mm CTV-PTV expansion) was used for all five pre-hydrogel and post-hydrogel plans (per the NSABP-B-39/RTOG-0413 protocol). For a second set of plans, standard margins were used for the prehydrogel plans, but reduced margins (a 10 mm GTV-CTV expansion and a 5 mm CTV-PTV expansion) were used for the post-hydrogel plans.

Intensity modulated radiotherapy (IMRT) treatment planning was performed using five, non-coplanar beams designed to minimize normal structure radiation exposure. Non-target structures included the ipsilateral and contralateral lungs, the heart, and the ipsilateral breast tissue not included in the PTV (breastNotPTV). Ipsilateral breast tissue was defined as that tissue lying within standard, whole-breast tangent beams (per the NSABP-B-39/RTOG-0413 protocol). Appropriate dose-volume objectives were assigned to these structures, and plans were considered acceptable when the following constraints were achieved: breastNotPTV V50%<50%, ipsilateral lung V30%<15%, and heart V5%<40%.

When using standard margin expansions, the hydrogel tended to increase normal tissue radiation doses. Five-field, partial-breast radiation treatment plans were generated for each of the five lumpectomy procedures; one plan was generated before hydrogel injection and a second plan was generated after hydrogel injection. As expected, both the lumpectomy cavity and the PTV were larger after hydrogel placement and normal tissue doses were modestly increased. With hydrogel injection, mean cavity volume increased from 15.7 to 41.4 cc, a change of 25.7 cc (95% confidence interval 7.8 to 43.7 cc). The mean PTV volume increased from 471.9 to 562.7 cc, a change of 90.8 cc (95% confidence interval 26.3 to 155.2 cc). While the mean cavity volume almost tripled, the fractional increase in the PTV size was much more modest (increasing only 19%). As seen in FIG. 5, the hydrogel tended to expand the cavity outward, away from the chest wall, but not laterally. As the CTV expansion is limited to remain within the breast tissue, there was therefore little net effect on the PTV size. Normal-tissue dosimetric parameters from all 5 lumpectomies are presented in FIG. 6; overall, when using standard treatment margins (25 mm), the hydrogel tended to increase normal tissue doses. The breast (non-PTV) V50% increased in 4 of 5 cases; the mean increase was 1.4% (95% confidence interval −1.7% to 4.5%). This increase was modest compared with the volume constraint of 50%. The ipsilateral lung V30% also increased in 4 of 5 cases. The increases were more sizable relative to the volume constraint of 15% (mean increase was 1.7%, 95% confidence interval −0.4% to 3.8%). As anticipated, the deeper, larger cavities resulted in higher lung doses; in one case, the post-hydrogel plan reached the ipsilateral lung V30% limit of 15%. For all three left sided lumpectomies, the hydrogel increased the heart V5%. But, in all cases, the volumes remained well under the 40% constraint (mean increase 3.1%, 95% confidence interval −3.0% to 9.2%).

When using reduced margin expansions, the hydrogel tended to decrease normal tissue radiation doses. The reduced margins were made feasible by the hydrogel's improved cavity visibility. As the hydrogel improves visualization of the lumpectomy cavity, its impact on normal-tissue doses was also examined when smaller margin expansions were employed. Reduced margins may be appropriate due to reduced uncertainty in target definition and also reduced day-to-day target localization error. With reduced treatment margins (a 10 mm GTV-CTV expansion and a 5 mm CTV-PTV expansion), the hydrogel tended to decrease normal tissue doses despite the increase in lumpectomy cavity volume (compared with no hydrogel and standard, 25 mm margins) (FIG. 7). The breast (non PTV) V50% decreased in all five cases (mean change −3.2%, 95% confidence interval −6.4% to 0.0%). The ipsilateral lung V30% also decreased in 4 of 5 cases (mean change −1.5%, 95% confidence interval −4.1% to 1.1%). For all left-sided lumpectomies, the heart V5% showed small decreases (mean change −0.8%, 95% confidence interval −2.3% to 0.8%).

Example 3

Radioopaque Hydrogels and Imaging

Figure 8:
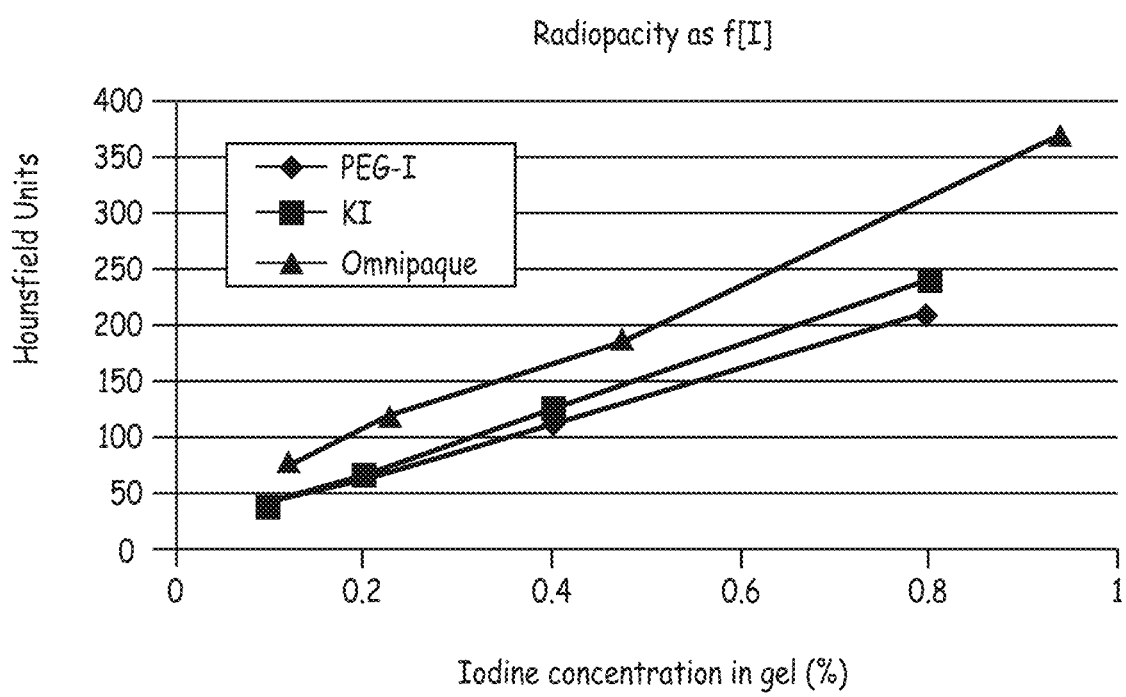
FIG. 8 is a plot of radiopacity as a function of iodine concentration, with an iodinated polyethylene glycol (PEG-I), potassium iodide (KI) and iodine (OMNIPAQUE) being compared.

The radiopacity of serial diluted Iohexol (OMNIPAQUE) was measured to obtain a CT number as a function of iodine concentration. A CT number (also referred to as a Hounsfield unit or number) is the density assigned to a voxel in a CT (computed tomography) scan on an arbitrary scale on which air has a density −1000; water, 0; and compact bone +1000. The CT number of diluted Iohexol ranged from 2976 at a 50% concentration, to 37 at a 0.2% concentration. These corresponded to a plot of iodine concentration versus CT number, with an iodine concentration of approximately 0.15% resulting in a CT number of about 90 (FIG. 8). Two different matrix formulations containing iodine at different concentrations were tested. First, iodine with succinimidyl glutarate (SG or SGA) functional terminal groups were complexed to 5000 Dalton linear PEG to make a PEG molecule complexed with iodine (PEG-I). Second, potassium iodide (KI) was incorporated into the gel at different concentrations.

Iodine Incorporation into the PEG Molecule

A PEG SG (with an SG count of 2.3 per molecule) containing an iodine core was synthesized. The PEG-I molecule was 6400 Daltons, of which iodine was 381 Daltons (5.9%). Thus, for example, with this iodine content, the percent solids of PEG-I in hydrogel that resulted in 0.1% and 0.2% iodine concentration in the resultant matrix was 1.68 and 3.36%. Table II shows how PEG-I concentrations can be manipulated to obtain a percentage iodine content, which in turn can be related to a CT number.

TABLE II

The percent solids of PEG-I in hydrogel, and the corresponding percent iodine concentrations.

| % iodine | % PEG-I in gel |
|---|---|
| 0.1 | 1.68 |
| 0.2 | 3.36 |
| 0.4 | 6.72 |
| 0.8 | 13.45 |

During sample preparation it was noted that the samples with high PEG-I concentrations gelled slowly, or not at all (Table III). This was observed at PEG-I concentrations up to about 20%. The potential reasons for this include crosslink interference due to SG end group proximity to the iodine hydrophobic core, rapid hydrolysis of the end groups prior to polymerization, or the formation of micelles due to the hydrophobic region, that may or may not have polymerized.

TABLE III

Hydrogel samples evaluated *.

| ID | Description | Condition |
|---|---|---|
| 1 | 0.1% I, 1.68% PEG-I, 13.32% 4a20kSGA | Gel |
| 2 | 0.2% I, 3.36% PEG-I, 11.64% 4a20kSGA | Gel |
| 4 | 0.8% I, 13.45% PEG-I, 1.55% 4a20kSGA | Liquid |
| 5 | 0.1% I, 10% 4a20kSGA, 0.120% KI | Gel |
| 6 | 0.2% I, 10% 4a20kSGA, 0.241% KI | Gel |
| 7 | 0.4% I, 10% 4a20kSGA, 0.481% KI | Gel |
| 8 | 0.8% I, 10% 4a20kSGA, 0.963% KI | Gel |
| 9 | 4% 10 µm MSs, 10% 4a20kSGA | Gel |

*PEG-I refers to a PEG with a covalently attached iodine; MSs refers to microspheres; branched PEG molecules are described as NaXXkYYY, with N being the number of arms, XX being the MW in thousands, and YYY indicating the functional group at the arms' termini for those arms not terminating in an iodinated groups. Thus 4a20kSGA refers to a 4-armed PEG of approximately 20,000 MW with SGA termini.

Free Iodine Incorporation into the Gel

Potassium iodide (KI) was also loaded into certain hydrogels. KI is 231.3 Daltons, and iodine is 192.2 Daltons (83.1%) so that the concentration of KI required to obtain the same iodine concentrations could be calculated. 0.1% iodine is 0.120% KI, 0.2% iodine is 0.241% KI, and 0.8% iodine is 0.963% KI.

Microsphere Incorporation into the Gel

A 4% microsphere loading was used. When loaded into microspheres at a concentration of 20%, then the iodine concentration in hydrogel, given a 4% microsphere loading in the hydrogel, is about 0.8%. The microspheres were made as described above.

Methods

Non-sterile rods of gel with either 0.1, 0.2, 0.4 or 0.8% incorporated iodine were created by injecting 5 ml of in situ gelling polymer into 10 ml syringes, creating plugs approximately 13.5 mm diameter and 30 mm length. Conditions were controlled to prevent gel hydrolysis prior to testing.

Gel samples underwent computed tomography imaging while still in syringes such that CT number was determined. Syringes were placed on the CT couch (long axis of the gel samples aligned with the couch). The following CT scanner and scan settings were used: Philips BRILLIANCE BIG BORE CT simulator, slice thickness 3 mm, 120 kVp, 300 mA, FOV 60 cm. Gels were removed from syringes by blowing them out with air from a 20 ml syringe. Following removal the gel plugs were weighed. Following imaging samples were placed in 150 ml containers, each containing 100 ml of PBS, and stored at room temperature prior to additional testing.

CT Imaging

CT Imaging showed a difference in radiopacity. As shown in FIG. 8, both iodine loading methods produced similar results, with a linear HU response to iodine concentration. These data have a similar slope to that obtained earlier with Iohexol (OMNIPAQUE), although there was a slight offset.

Example 4

Radiopacity of Hydrogel with Bound Iodine

This example describes the radiopacity of different levels of triodoo benzoate (TIB) loading, along with different hydrogel percent solids. The evaluated materials and their estimated (based on Example 1) Hounsfield Units (HU) are shown in Table VI. Hydrogel plugs were created inside silicone tubing of 0.375 inch ID and placed in conical tubes to prevent evaporation. An 8a20kSGA PEG with 3-4 terminal TIB (31% substitution) or about 5 terminal TIB (61% substitution) was reacted with trilysine to make the gels. A neutral hydrogel pH was used prevent excess hydrolysis prior to testing. There was fairly good agreement between the estimated radiopacity and that actually measured at time zero.

TABLE VI

The four different hydrogels evaluated, along with their iodine concentration [I] and radiopacity (HU).

| | % of PEG arms with TIB attachments | |
| --- | --- | --- |
| | 31% TIB substitution | 61% TIB substitution |
| 5% Solids hydrogel | Hydrogel [I]: 0.21%<br>Estimated HU: 100 | Hydrogel [I]: 0.35%<br>Estimated HU: 155 |
| 10% Solids hydrogel | Hydrogel [I]: 0.42%<br>Estimated HU: 180 | Hydrogel [I]: 0.70%<br>Estimated HU: 280 |

Following the initial radiopacity measurements, samples were taken from the syringes and placed in conical tubes containing tap water. Samples were stored at room temperature (RT), and at each time point the samples were removed from the vials, weighed, and rescanned. The radiopacity (RO) over time, without correction for swelling, is shown in FIG. 9. The radiopacity corrected for swelling is shown in FIG. 10. This data demonstrates some important features. First, the sample swelling demonstrates ongoing hydrolysis, showing that the tested formulation will eventually liquefy, and if implanted, will absorb. Second, when corrected for swelling, the data demonstrates that the iodine is remaining bound to the precursor. This latter observation shows that radiopacity may be maintained throughout the lifetime of the implant if desired.

Example 5

Osmotic Agents for Injectable Slurries

Figure 11A:
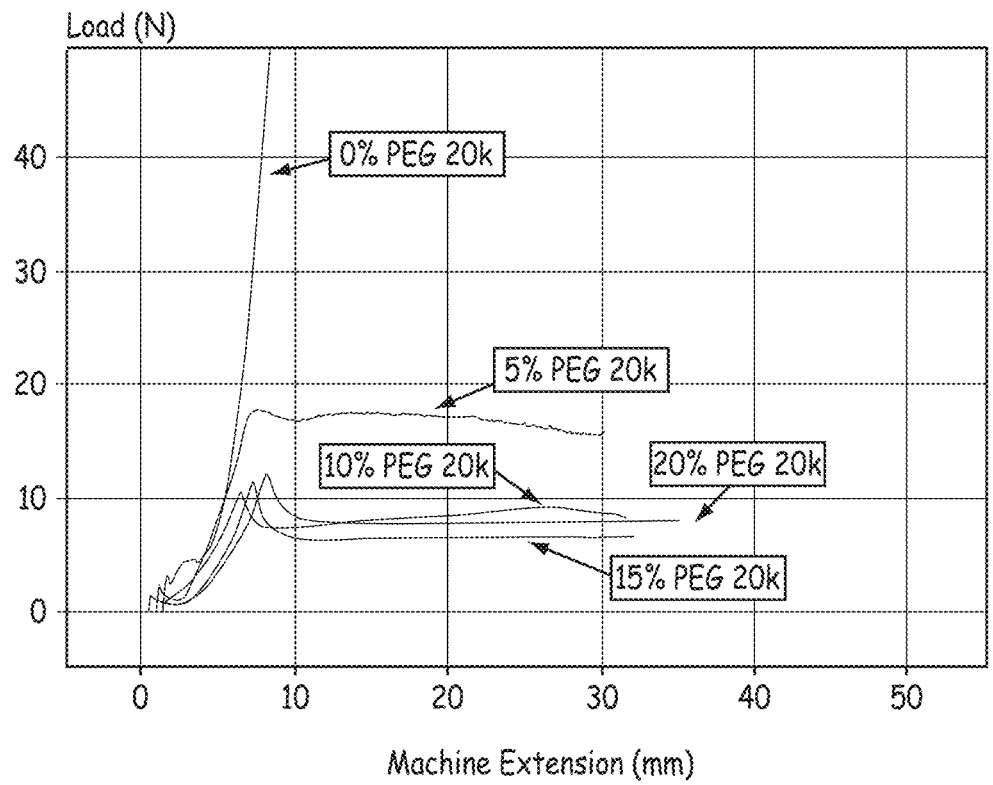
FIG. 11A shows how an osmotic agent may be used to reduce the force required to eject a collection of particles from a small gauge needle.

The addition of osmotic agents was observed to reduce the force required to move the particles through a small opening. The use of linear polymers contributed viscosity and, without being bound to a particular theory, a thixotropic effect. FIG. 11A is a plot of results of a slurry injection force testing trial. Solutions of covalently crosslinked multiarmed PEG hydrogel particles of about 70 micron diameter were formulated in 28% free water with different concentrations of linear PEG (20 k molecular weight). Materials were injected using a 3 cc syringe and 18 gauge 15 cm needle, with the force being monitored and reported in N.

Figure 11B:
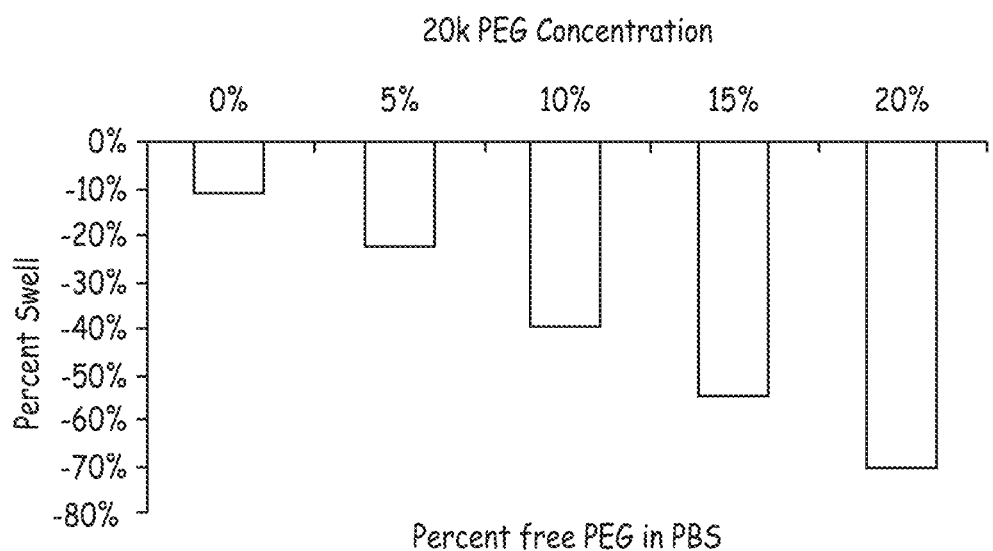
FIG. 11B depicts shrinkage of hydrogels in the presence of the osmotic agents of FIG. 11A.

FIG. 11B shows shrinkage in solutions of PEG. Covalently crosslinked multiarmed PEG hydrogel plugs were made as described and exposed for 24 hrs in 37° C. phosphate buffered solution (PBS, a physiological saline) containing 20 k linear PEG at different concentrations as indicated. The plugs were observed to shrink (negative swelling), and 20% PEG solution caused about 70% shrinkage.

Further Disclosure

An embodiment of the invention is a pharmaceutically acceptable implant system or kit comprising a collection of pharmaceutically acceptable, covalently-crosslinked hydrogel particles having a radioopaque agent covalently attached to a plurality of the particles in the collection, with the radioopaque agent being present in the collection at a concentration of at least about 0.1% w/w. Another embodiment is a process for making an implantable system comprising preparing a hydrogel matrix comprising covalently attached radioopaque agents and breaking the matrix into a collection of pharmaceutically acceptable, covalently-crosslinked hydrogel particles. Another embodiment is a pharmaceutically acceptable implant system or kit comprising a collection of pharmaceutically acceptable, covalently-crosslinked hydrogel particles that comprises a plurality of sets of the particles, with the sets having different rates of biodegradation. Another embodiment is a method of treating a patient with a pharmaceutically acceptable implant system comprising implanting a collection of pharmaceutically acceptable, covalently-crosslinked hydrogel particles. Another embodiment is a method for treating a tissue comprising placing a hydrogel in an iatrogenic site, wherein the hydrogel conforms to margins of the site and has a Hounsfield number of more than about 50. Another embodiment is a plurality of, or collection of, particles for use as: an implant, a spacer, a fiduciary marker, or an implant for a iatrogenic site.

These methods, processes, collections, hydrogels, particles, and systems may comprise, for example, one or more of the following features: the particle collection further comprising particles free of a covalently-bound radioopaque agent; the collection further comprising a non-covalently bound radioopaque agent; wherein the collection particles are spheroidal with a maximum diameter of between about 20 to about 200 microns, with the particles being biodegradable to produce only degradation products that are absorbed into the circulatory system and cleared from the body via renal filtration; with the particles being hydrolytically biodegradable; wherein the particles, before hydrolysis, have a total swellability in physiological solution of no more than about 30% by volume; wherein the degradation products comprise a polyethylene glycol covalently bound to the radioopaque agent, with the radioopaque agent comprising iodine; wherein the polyethylene glycol is a branched polyethylene glycol with at least four arms; wherein between 25% and 90% of the arms comprise the radioopaque agent; with the collection having a lubricity and maximum diameter for manual passage out of a syringe through a 30 gauge needle; further comprising an osmotic agent that comprises a linear hydrophilic polymer, with the agent present in a mixture with the collection; wherein the collection of particles is completely biodegradable at a time between about 30 and about 365 days; wherein the collection comprises a plurality of sets of the particles, with the sets having different rates of biodegradation; wherein a first set of the particles is biodegradable within about 8 to about 12 days and a second set of the particles is degradable within about 45 to about 55 days; wherein the particles are hydrolytically degradable; further comprising an applicator, with the particles being disposed in the applicator; wherein the particles are dehydrated; further comprising a container of physiological saline fluidly connectable to the applicator to mix the saline and particles in the applicator; further comprising a therapeutic agent; further comprising a radiation source; wherein the spacer or matrix is formed from a first precursor comprising a plurality of first functional groups and a second precursor comprising a plurality of second functional groups, with the first functional groups forming covalent bonds with the second functional groups to thereby form the matrix; wherein at least one precursor further comprises the radioopaque agent; wherein the particles are prepared by grinding, milling, chopping, micellar polymerization, or emulsion polymerization; wherein a first set of the particles is biodegradable within about 8 to about 12 days and a second set of the particles is degradable within about 45 to about 55 days; a set of particles that is biodegradable within about 60 to about 90 days; wherein the particles are hydrolytically degradable; comprising a plurality of the particles having a covalently attached radioopaque agent, with the radioopaque agent being present in the collection at a concentration of at least about 0.1% w/w; wherein the particles are formed from a first precursor comprising a plurality of first functional groups and a second precursor comprising a plurality of second functional groups, with the first functional groups forming covalent bonds with the second functional groups to thereby form the matrix, with at least one of the precursors comprising polyethylene glycol; wherein at least one of the precursors comprises a polyethylene glycol having a plurality of branches terminated with triiodobenzoate; a plurality of the particles having a covalently attached radioopaque agent, with the radioopaque agent being present in the collection at a concentration of at least about 0.1% w/w; placing the collection between two tissues and preparing a radiation treatment plan that comprises a therapeutic dose of radiation to treat a cancer in one of the tissues; comprising placing the collection in a tissue for augmentation; with the hydrogel further comprising a radioopaque agent; introducing a liquid comprising a hydrogel precursor into the site that flows into the site and reacts in the site to form the hydrogel as a covalently crosslinked continuous phase that adheres to the margins; comprising a second precursor that reacts with the first precursor to form covalent bonds to form the hydrogel; wherein the precursor comprises a covalently bound radioopaque agent; wherein the radioopaque agent comprises iodine; wherein the precursor comprises a branched polyethylene glycol, with the radioopaque agent being disposed on at least one of the branches; further comprising substantially filling the site with the hydrogel; wherein the hydrogel is biodegradable; forming a radiation plan based on the hydrogel as a fiducial marker; wherein the plan sets forth margins of less than about 20 mm; wherein the hydrogel comprises a collection of covalently-crosslinked hydrogel particles; wherein the a collection of hydrogel particles comprises a radioopaque agent covalently attached to a plurality of the particles in the collection, with the radioopaque agent being present in the collection at a concentration of at least about 0.1% w/w.

Various embodiments of the invention have been set forth herein. In general, features of the various embodiments may be mixed and matched for further combinations that are not explicitly detailed. Headings are set forth only for organizational purposes and do not limit the scope of the disclosure.

The invention claimed is:

1. A method for placement of a pharmaceutically acceptable implant into a patient comprising
delivering a pharmaceutically acceptable implant through an applicator into the patient at a selected placement site, the implant comprising a flowable, hydrolytically biodegradable polymer composition, an osmotic agent, and a therapeutic agent, wherein the flowable, hydrolytically biodegradable polymer composition comprises a collection of covalently-crosslinked hydrolytically biodegradable hydrogel particles, a hydrogel precursor composition that reacts to form covalent bonds at physiological conditions with the product being a covalently-crosslinked hydrolytically biodegradable hydrogel, or a combination thereof, wherein the implant at the selected placement site is visible under ultrasound, and wherein the therapeutic agent is released from the implant at the placement site.

2. The method of claim 1 further comprising monitoring the delivering of the implant to the placement site with ultrasound.

3. The method of claim 1 wherein the implant further comprises a pharmaceutically acceptable fluid and wherein the implant is delivered to the placement site as a slurry.

4. The method of claim 1 wherein the applicator comprises a syringe, a catheter, a needle, a double barreled container, or combinations thereof.

5. The method of claim 1 wherein the applicator comprises a syringe connected to a needle, and the delivering of the implant comprises injecting the implant through the needle into the placement site.

6. The method of claim 1 wherein the hydrogel particles have an average diameter from about 10 microns to about 500 microns.

7. The method of claim 1 wherein the hydrogel particles have an average diameter from about 125 microns to about 500 microns.

8. The method of claim 1 wherein the implant comprises an ultrasound contrast agent.

9. The method of claim 1 wherein the implant further comprises a radiopaque agent.

10. The method of claim 9 wherein the radiopaque agent is covalently attached to the polymer composition.

11. The method of claim 1 wherein the therapeutic agent comprises a pain reliever, an anesthetic, a steroid, a chemotherapeutic agent, or combinations thereof.

12. The method of claim 1 wherein the implant is adherent to a tissue at the placement site.

13. The method of claim 1 wherein a volume of the implant after delivering at the placement site is no more than 50% more than a volume of the implant prior to delivering at the placement site and wherein the porosity is more than 30%.

14. The method of claim 1 wherein the implant has a time for degradation from about 7 days to about 180 days.

15. The method of claim 1 wherein the implant is hydrolytically biodegradable to produce degradation products that are absorbed into the circulatory system and cleared from the body via renal filtration.

16. The method of claim 1 wherein the collection comprises dehydrated covalently-crosslinked hydrolytically biodegradable hydrogel particles.

17. The method of claim 1 further comprising visualizing an interface of the implant and a tissue with ultrasound, X-ray, or a combination thereof.

18. The method of claim 1 further comprising a step of mixing the polymer composition and the osmotic agent with the therapeutic agent to form the implant.

19. The method of claim 1 wherein the osmotic agent comprises polyethylene glycol.

20. The method of claim 1 wherein the therapeutic agent comprises particulates.

21. The method of claim 1 wherein the implant comprises gas microbubbles, microparticles comprising the therapeutic agent, hydrophobic microdomains, hydrogel particles, and/or microparticulates of the therapeutic agent.

22. The method of claim 1 wherein the placement site is between a first tissue location and a second tissue location.

23. The method of claim 1 wherein the placement site is a muscle tissue location and/or a nerve tissue location.

* * * * *

UNITED STATES PATENT AND TRADEMARK OFFICE
CERTIFICATE OF CORRECTION

PATENT NO. : 11,083,802 B2
APPLICATION NO. : 16/817291
DATED : August 10, 2021
INVENTOR(S) : Campbell et al.

Page 1 of 1

It is certified that error appears in the above-identified patent and that said Letters Patent is hereby corrected as shown below:

On the Title Page

Column 1, under "Related U.S. Application Data", delete "(60)" and insert -- (63) --, therefor.

On Page 3, Column 2, Item (56), under "OTHER PUBLICATIONS", Line 38, delete "Microsphers" and insert -- Microspheres --, therefor.

On Page 3, Column 2, Item (56), under "OTHER PUBLICATIONS", Line 42, delete "Bull Mater Sci," and insert -- Bull. Mater. Sci., --, therefor.

On Page 3, Column 2, Item (56), under "OTHER PUBLICATIONS", Line 43, delete "Microsphers" and insert -- Microspheres --, therefor.

On Page 3, Column 2, Item (56), under "OTHER PUBLICATIONS", Line 59, delete "Biomacromoloecules," and insert -- Biomacromolecules, --, therefor.

In the Claims

In Column 36, Claim 1, Line 29, delete "comprising" and insert -- comprising: --, therefor.

Signed and Sealed this
Twenty-ninth Day of March, 2022

Drew Hirshfeld
*Performing the Functions and Duties of the
Under Secretary of Commerce for Intellectual Property and
Director of the United States Patent and Trademark Office*